(12) United States Patent
Pawlowski et al.

(10) Patent No.: US 12,311,071 B2
(45) Date of Patent: May 27, 2025

(54) CASH SANITIZATION OR STERLIZATION DEVICE

(71) Applicant: BAKIN GLOBAL, LLC, Redondo Beach, CA (US)

(72) Inventors: Ian Pawlowski, Gardena, CA (US); Tristen Rivera, Los Angeles, CA (US)

(73) Assignee: Bgkin Global LLC, Redondo Beach, CA (US)

( * ) Notice: Subject to any disclaimer, the term of this patent is extended or adjusted under 35 U.S.C. 154(b) by 540 days.

(21) Appl. No.: 17/665,302

(22) Filed: Feb. 4, 2022

(65) Prior Publication Data

US 2022/0257819 A1 Aug. 18, 2022

Related U.S. Application Data

(60) Provisional application No. 63/146,558, filed on Feb. 5, 2021.

(51) Int. Cl.
| | |
|---|---|
| *A61L 2/24* | (2006.01) |
| *A61L 2/10* | (2006.01) |
| *B65G 13/06* | (2006.01) |
| *B65G 23/08* | (2006.01) |

(52) U.S. Cl.
CPC ............... *A61L 2/24* (2013.01); *A61L 2/10* (2013.01); *B65G 13/06* (2013.01); *B65G 23/08* (2013.01)

(58) Field of Classification Search
CPC .......... A61L 2/10; A61L 2/24; A61L 2202/11; A61L 2202/14; A61L 2202/16; A61L 2202/24; A61L 2202/121; A61L 2202/122
See application file for complete search history.

(56) References Cited

U.S. PATENT DOCUMENTS

| | | | | |
|---|---|---|---|---|
| 2019/0290791 | A1* | 9/2019 | Baker | A61B 90/70 |
| 2021/0330832 | A1* | 10/2021 | Dobbins | G07F 9/10 |
| 2021/0338866 | A1* | 11/2021 | Grenon | G01J 1/429 |

* cited by examiner

*Primary Examiner* — David E Smith
*Assistant Examiner* — Hsien C Tsai

(57) ABSTRACT

A cash sterilization device, includes a sterilization device case, the sterilization device case having an opening on one side and a cap assembly; an internal sterilization assembly, the internal sterilization device including an opening, wherein the internal sterilization is inserted into the opening of the sterilization device case, the cap assembly is attached to cover the internal sterilization within the sterilization device case, and wherein the opening of the sterilization device case is aligned with the opening of the internal sterilization assembly.

10 Claims, 28 Drawing Sheets

DC Input Port 1005

Insertion Plate 1015

Switching Assembly 1010

DC Input Port 1005

US 12,311,071 B2

CASH SANITIZATION OR STERLIZATION DEVICE

RELATED APPLICATIONS

This application claims priority to and is related to application Ser. No. 63/146,558, filed Feb. 5, 2021, the disclosure of which is incorporated by reference in its entirety.

BACKGROUND

The current Covid-19 pandemic has shown the need for business owners and consumers to be more sanitary in their interactions and/or operations. Many of these businesses still utilize cash in their business transactions. Cash is an extremely dirty currency in that it may touch multiple individual's hands (which increases the chance of the transferring of bacteria, viruses and/or germs. Accordingly, cash is a breeding ground for bacteria, viruses and/or germs. Grocery stores, casinos, convenience stores, banks or other financial institutions and/or restaurants still handle a large volume of cash currency. Accordingly, there is a need to clean, sanitize and/or sterilize cash paper bills to eliminate and/or significantly reduce the bacteria, viruses and/or germs present thereon.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

Figure 1A:
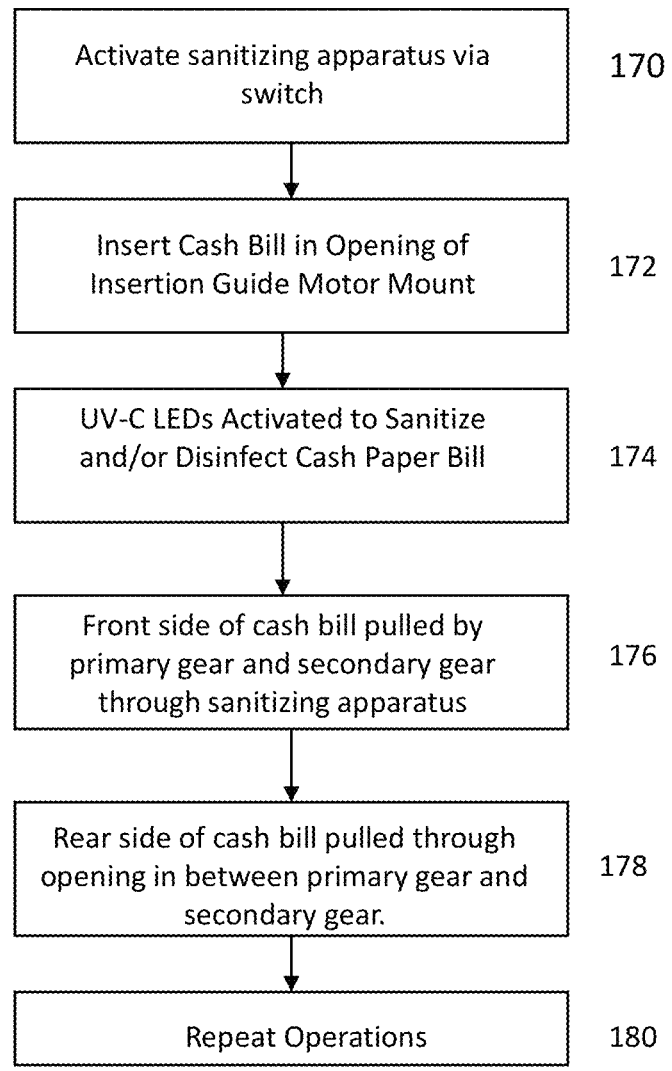
FIG. 1A illustrates a flowchart of operation of a cash paper bill sanitization device according to some embodiments.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

A cash sanitization or sterilization device is described herein which receives in cash paper bills on one side or end of the device, sanitizes and/or sterilizes the cash paper bills utilizing ultraviolet-C (UV-C) light, and then returns sanitizes cash paper bills on an opposite side or end of the cash sanitation device. In some embodiments, the cash sanitization device can process and clean 20 cash paper bills a minute, or alternatively between 10 and 60 cash paper bills a minute. The compact size of the cash sanitization devices is also one of the important and novel features of these embodiments. Although the cash sanitization device is shown as a standalone device in the drawings presented below, the cash sanitization device (or major components of it) may be integrated into other devices that handle large volumes of cash, such as an Automated Teller Machine (e.g., ATM), a paper bill change machine, a currency counter device, a currency counterfeit detector device, or other similar devices. In these cases, the insertion plate or section of the cash sanitization device may be changed in order to interface with the existing equipment, the power and/or switching assembly may be controlled by the ATM or change machine, and the cash paper bill may be held in a reservoir or other holding area within the ATM or change machine, rather than exiting the device, as is the cash sanitization device described below. In some embodiments, the cash sanitization device (and/or some of the components thereof) may be utilized to disinfect and/or sterilize other currency and/or payment cards (e.g., debit cards, credit cards, or gift cards). In some embodiments, the cash sterilization device may sterilize other paper money representations besides cash bills that are distributed to users. For example, vouchers may be distributed to users. The cash sterilization device may be utilized to sterilize and/or disinfect these paper cash vouchers. In these cases, the machine may be smaller in footprint because the other currency and/or payment cards are smaller and the UV-C lights need to disinfect the other currency and/or payment cards. In these embodiments, the number of LEDs in the LED fixture may also be varied because of the smaller size of the payment cards and/or currency. The embodiments described herein are directed to a cash sterilization device that is easy to assemble and/or manufacture and/or easy to repair because the cash sterilization device is modular and compact. Similarly, the embodiments described herein are directed to a compact sterilization device that is easy to integrate because of the small footprint.

FIG. 1A illustrates a flowchart of operation of a cash paper bill sanitization device according to some embodiments. Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step. In some embodiments, in step 170, a switch may activate the cash paper bill sanitization device. In some embodiments, in step 172, a cash paper bill may be inserted into an opening of an insertion guide motor mount. In some embodiments, a thermoresistor or another sensor may sense the presence of the cash paper bill. In some embodiments, the sensing by the thermoresistor or other sensor of the cash paper bill may turn on and/or activate the plurality of UV-C LEDs. In some embodiments, in step 174, a plurality of UV-C LEDs may be activated to sanitize and/or disinfect the inserted cash paper bill. In some embodiments, in step 176, the primary gear is engaged (which engages the secondary gear) and a front side of the cash bill is pulled by the primary gear and secondary gear through the cash paper bill sanitization apparatus. In some embodiments, in step 178, the rear side of the cash paper bill is pulled through the opening in between the primary gear and the secondary gear. In some embodiments, in step 180, the steps 172 through 178 are repeated for any cash paper bill pulled inserted into the opening in the insertion guide motor mount. In some embodiments, the cash paper bill may be fed through the insertion guide to the gears and the gears may pull the cash paper bill through the device.

Figure 1B:
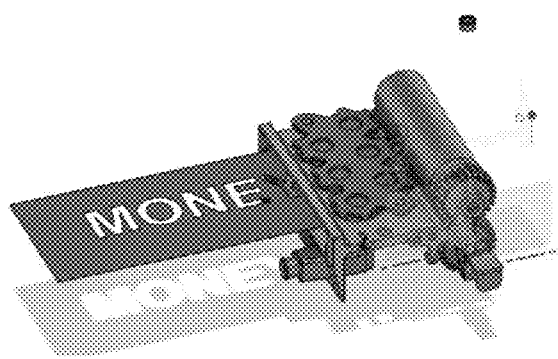
FIG. 1B illustrates the cash paper bill being inserted into the cash sanitization or sterilization device.
Figure 1C:
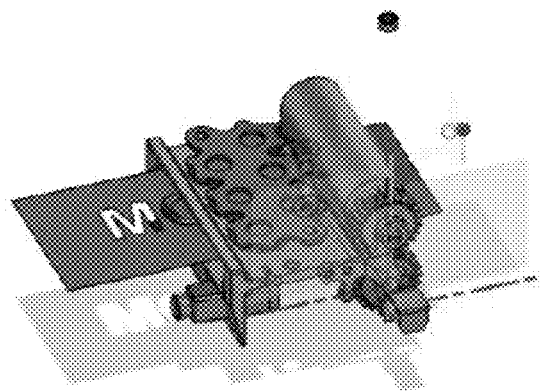
FIG. 1C illustrates the cash paper bill progressing through the insertion plate and having a portion of the cash paper bill being irradiated by the UV-C LEDs.
Figure 1D:
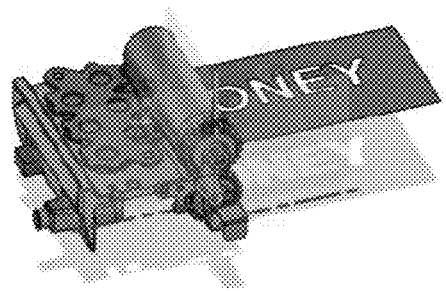
FIG. 1D illustrates a portion of the cash paper bill exiting between the primary roller and the secondary roller of the cash sanitization device.
Figure 1E:
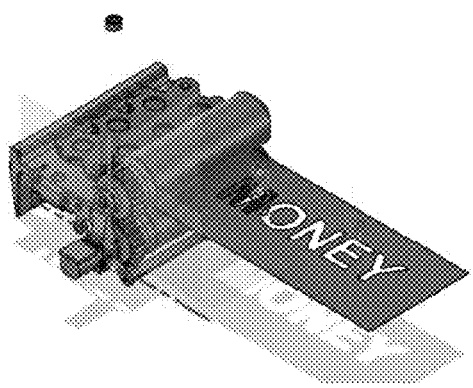
FIG. 1E illustrates when the entire cash paper bill exits the cash sanitization device.

FIG. 1B-1E illustrates the movement of the cash paper bill through a cash sanitization device. FIG. 1B illustrates the cash paper bill being inserted into the cash sanitization or sterilization device. FIG. 1C illustrates the cash paper bill progressing through the insertion plate and having a portion of the cash paper bill being irradiated by the UV-C LEDs. FIG. 1D illustrates a portion of the cash paper bill exiting between the primary roller and the secondary roller of the cash sanitization device. FIG. 1E illustrates when the entire cash paper bill exits the cash sanitization device.

Figure 1F:
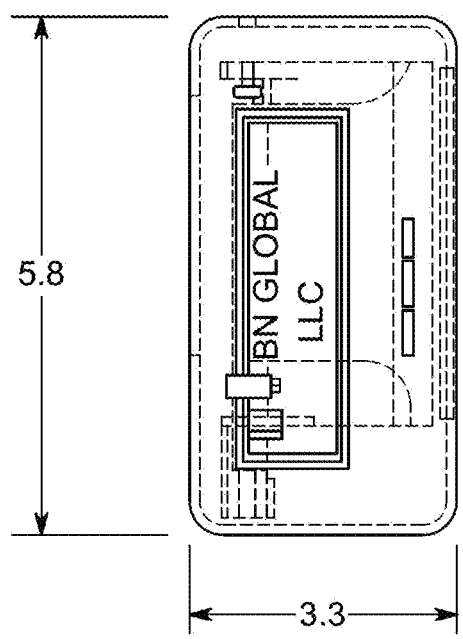
FIG. 1F illustrates a top view of the cash paper bill sanitization or sterilization device according to some embodiments.
Figure 1G:
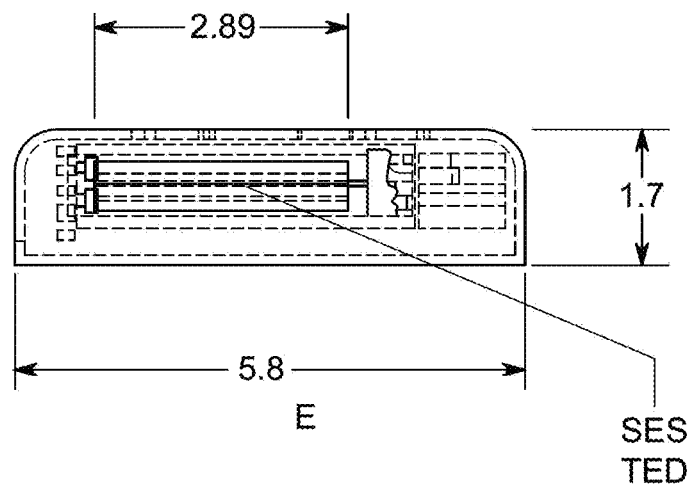
FIG. 1G illustrates a front view of the cash paper bill sanitization or sterilization device according to some embodiments.

FIG. 1F illustrates a top view of the cash paper bill sanitization or sterilization device according to some embodiments and FIG. 1G illustrates a front view of the cash paper bill sanitization or sterilization device according to some embodiments. As is illustrates in these Figures, the length of the cash paper bill sanitization or sterilization device may be 3.3 inches, and/or alternatively may range from 2 inches to 4.5 inches. In some embodiments, the width of the cash paper bill sanitization or sterilization device may be 5.8 inches, or alternatively may range from 4.0 inches to 7 inches. In some embodiments, the height of the cash paper bill sanitization or sterilization device may be 1.7 inches or may range from 1.0 inches to 3.0 inches. In some embodiments, the cash sanitization device may have a height of 2.108 inches, a depth of 3.132 inches and/or a width of 4.7491 inches.

Figure 2:
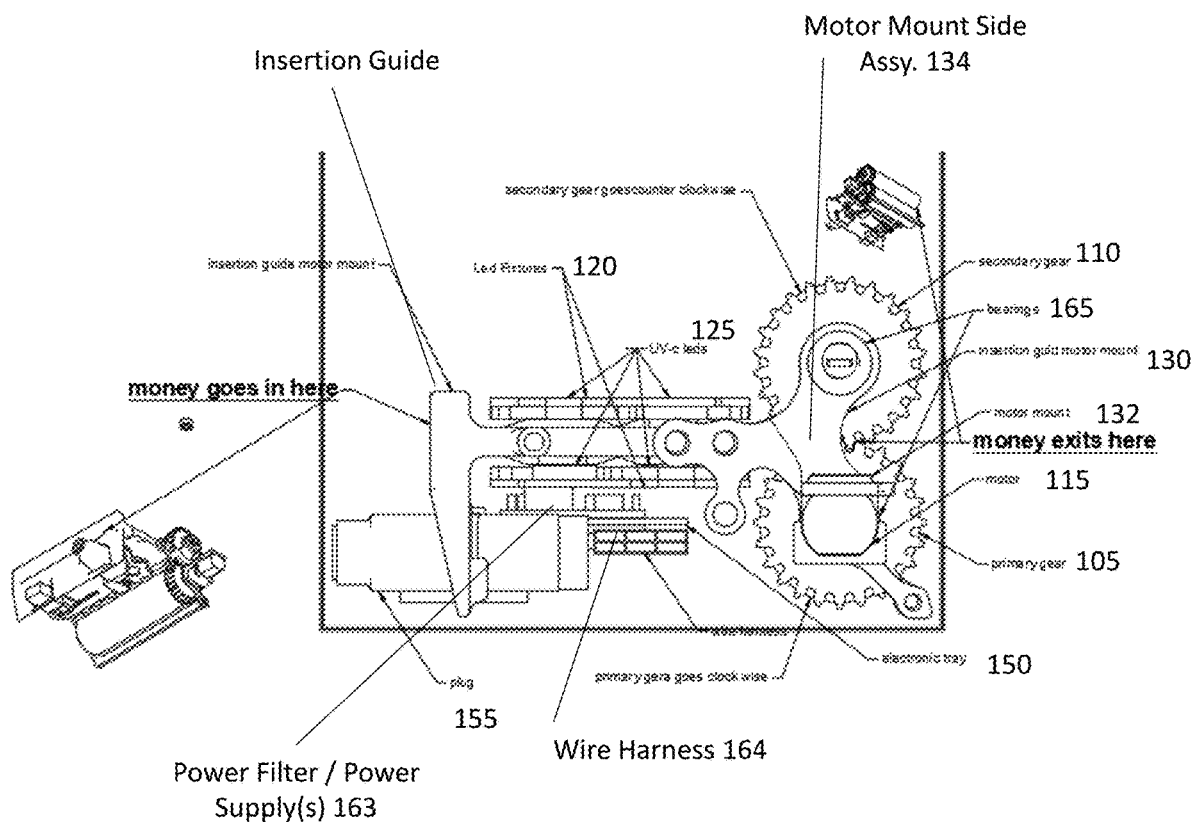
FIG. 2 illustrates a side view of a cash paper bill sanitization device according to some embodiments.

FIG. 2 illustrates a side view of a cash paper bill sanitization device according to some embodiments. In some embodiments, the cash paper bill sanitization device 100 includes the insertion guide motor mount 130. In some embodiments, the insertion guide motor mount 130 is the largest component of the cash paper bill sanitization device 100. In some embodiments, the cash paper bill sanitization device 100 may include a primary gear 105, a secondary gear 110, a motor assembly 115, a LED fixture assembly 120, a plurality of UV-C light emitting diodes (LEDs) 125, an insertion guide motor mount 130 (e.g., which may include an insertion guide 127, a main support plate 128 and a motor mount support bar (not shown)), a motor mount 132, a motor mount side assembly 134, a power filter/power supply board 163, a power harness 164, an electronics tray 150 assembly and/or (where the one or more power supplies are located along with power supply harness mount). The cash paper bill sanitization device 100 may also include a DC voltage input plug 155, a switch 160 (or switching assembly), one or more bearing bolts 166, a power supply filter 162 (to convert input DC power (e.g., 24 volts DC) to clean 3 to 24 volts DC power), one or more bearings 165 and/or wires or harnesses (not shown) to connect all electrical components to associated power supplies, switches and/or DC plugs.

Figure 3:
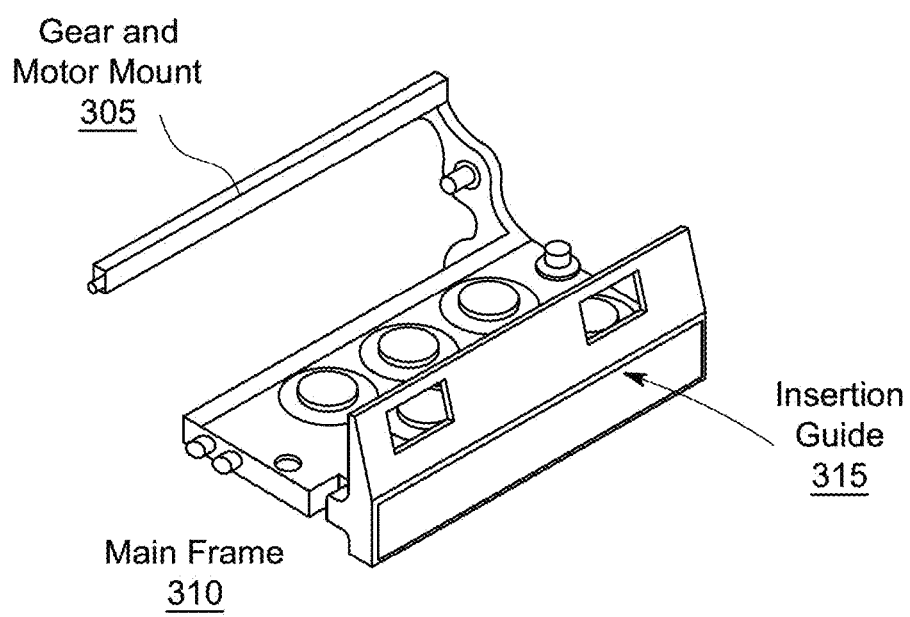
FIG. 3 illustrates an insertion guide motor mount according to some embodiments.

FIG. 3 illustrates an insertion guide motor mount according to some embodiments. In some embodiments, the insertion guide motor mount 130 may include a gear and motor mount or support assembly 305, a main support plate 310 and/or an insertion plate 315. In some embodiments, the gear and motor mount assembly 305 may allow the motor assembly and/or gear to be placed in proper position for operation. In some embodiments, the gear and motor mount assembly may be connected, and/or coupled to one end of the main support plate 310. In some embodiments, a first LED fixture may be connected to a top portion of the main support plate and a second LED fixture may be connected to a bottom portion of the main support plate 310. In some embodiments, the top portion of the main support plate 310 and the bottom portion of the main support plate 310 may be separate plates, or alternatively may be separate surfaces. In some embodiments, the main support plate 310 may have a width to allow paper bills to pass through (e.g., there is an opening between the top portion and the bottom portion of the main support plate 310). In some embodiments, a top surface of the main support plate 310 may have a plurality of holes or openings that correspond to the positioning of LEDs in the LED fixture. This allows the UV-C LEDs to shine on a large portion of both the top surface and the bottom surface of the cash paper bill and thus sanitize and disinfect the cash paper bill. In some embodiments, the insertion plate 315 is connected to a second and/or opposite end of the main support plate 310 as compared to gear and motor mount assembly 305. In some embodiments, the insertion plate 315 has openings for the DC plug, insertions of cash paper bill(s), a switching assembly, and/or other components. In some embodiments, the motor and gear mount 305 may be angled at approximately 45 degrees from the main support plate 310, or alternatively between 30 degrees and/or 60 degrees from the main support plate 310. In some embodiments, the insertion plate 315 has a vertical orientation with respect to the main support plate 310 (which is orientated in a horizontal direction or plane). In some embodiments, the insertion guide motor mount 130 has a width of approximately of 3.7 inches, a length of approximately 3.1 inches, and/or a height of approximately 1.7 inches. In alternatively embodiments, the width of the insertion guide motor mount 130 may range from 2.5 inches to 8.0 inches; the length of the insertion guide motor mount 130 may range from 2.5 inches to 3.6 inches, and the height of the insertion guide motor mount 130 may range from 1.2 inches to 2.2 inches. In some embodiments, the paper cash currency may be fed in sideways.

Figure 4:
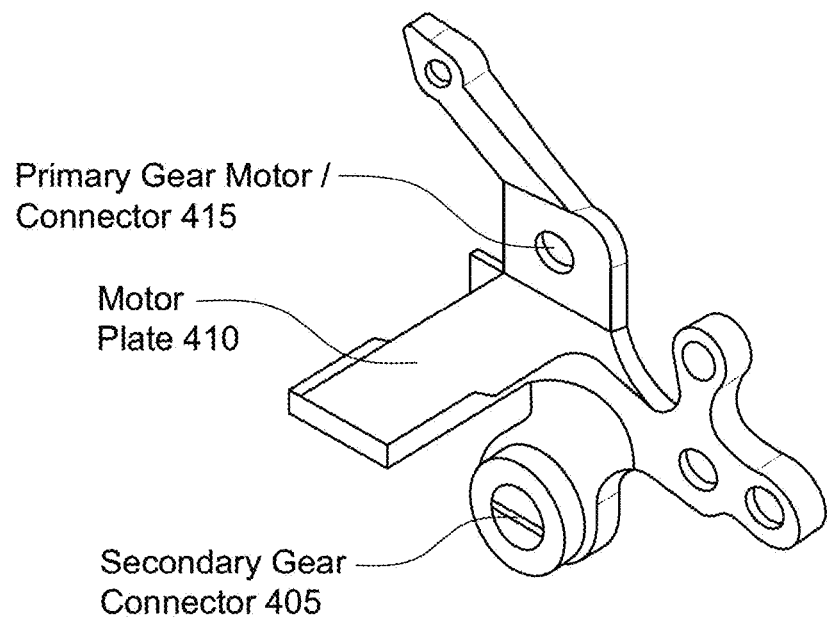
FIG. 4 illustrates a motor mount side assembly accordingly to some embodiments.

FIG. 4 illustrates a motor mount side assembly accordingly to some embodiments. In some embodiments, the motor mount side assembly 134 is connected, coupled and/or attached to a side or both sides of the insertion guide motor mount 130. In some embodiments, the motor mount side assembly 134 provides positioning and/or locates the one or more primary gears and/or the one or more secondary gears. In some embodiments, the motor mount side assembly 134 may also provide stability for the whole cash sanitization device 100. In some embodiments, the motor mount side assembly includes an opening or connector 405 for the secondary gears, a motor mount plate 410 and/or an opening or connector 415 for the primary gear to be connected and/or driven by the motor. In some embodiments, the opening or connector 405 for the secondary gear is located below the motor mount plate 410. In some embodiments, the motor mount plate 410 is flat to allow the motor to operate in a stable position. In some embodiments, the other side of the cash dispensing device may have a side assembly that also provides stability for the cash sanitization device. In some embodiments, the opposite side assembly just does not include a motor mount, but does provide support for an opposite side of the primary gear (opposite from the side where the primary gear is connected to the motor assembly. In some embodiments, the motor mount side assembly 134 may have a length of 1.5 inches, or alternately may range from a length of 1.0 inches to 2.0 inches. In some embodiments, the motor mount side assembly 134 may have a depth of 1.0 inches (for the motor assembly), or alternatively the depth of the motor mount side assembly may range from 0.5 inches to 1.5 inches.

Figure 5A:
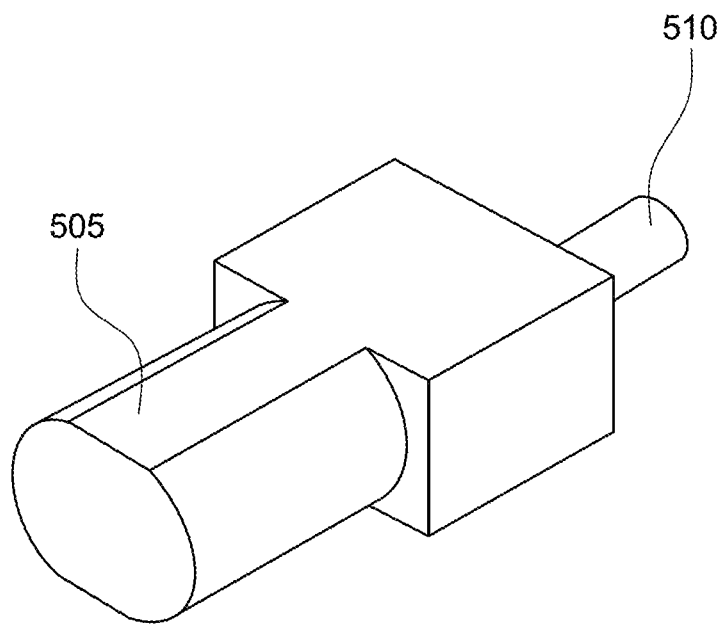
FIG. 5A illustrates a motor according to some embodiments.
Figure 5B:
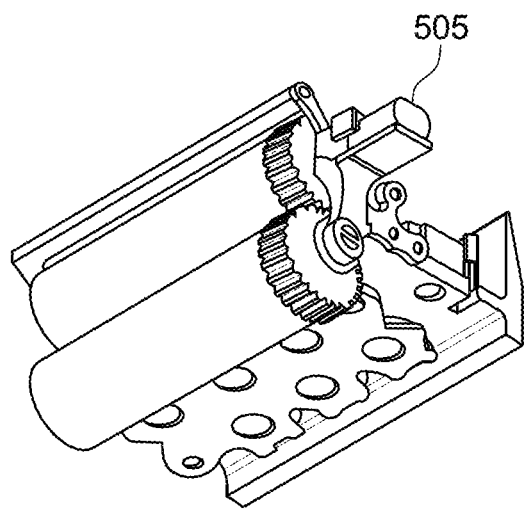
FIG. 5B illustrates a motor mounted on a motor mount plate according to some embodiments.

FIG. 5A illustrates a motor according to some embodiments. FIG. 5B illustrates a motor mounted on a motor mount plate according to some embodiments. In some embodiments, the motor 505 may be a 30 revolutions per minute 6 volt DC motor and may have a motor shaft 510. In some embodiments, the motor 505 may be a motor having up to 120 revolutions per minute (e.g., or ranging from 10 rpm to 300 rpm). In some embodiments, the motor 505 may be connected and/or adhered to the motor mount plate 410 and the motor shaft may be inserted into the opening or connector 415 that is connected or coupled to the primary gear. In this embodiment, the primary gear is positively engaged by the motor 505 (and motor shaft 510) and the primary gear drives the secondary gear. In some embodiments, the motor 505 may have the following dimensions (2.01×1.93×0.2 inches), but the motor dimensions may vary.

Figure 6A:
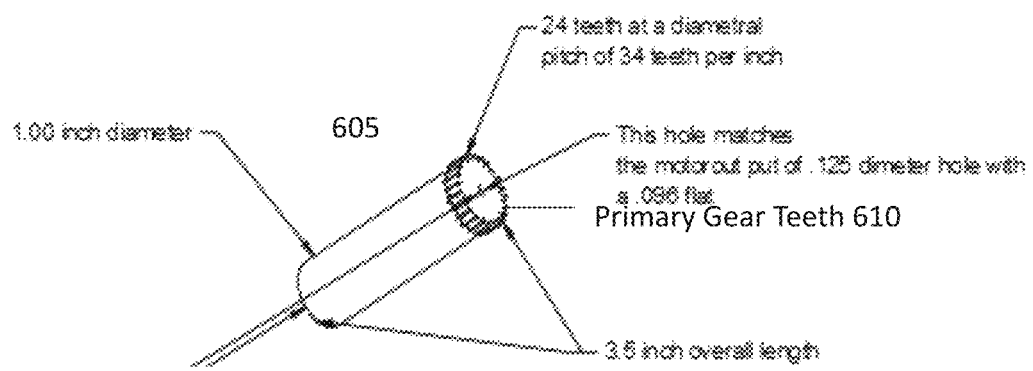
FIG. 6A illustrates a primary gear according to some embodiments.
Figure 6B:
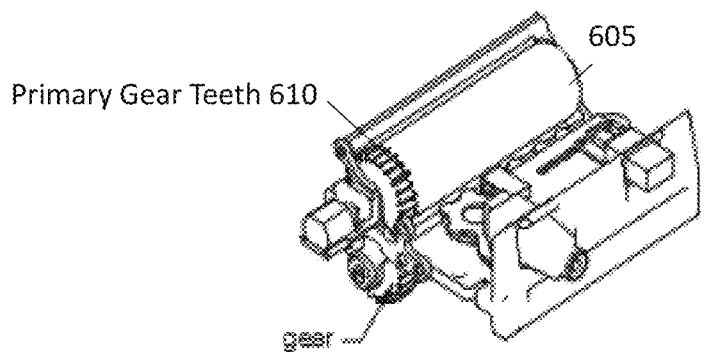
FIG. 6B illustrates a primary gears placement in a cash dispensing apparatus according to some embodiments.

FIG. 6A illustrates a primary gear according to some embodiments. FIG. 6B illustrates a primary gears placement in a cash dispensing apparatus according to some embodiments. In some embodiments, the primary gear includes the primary gear body 605 and the primary gear teeth. In some embodiments, the primary gear assembly also includes an opening and/or hole into which a motor shaft 510 may be inserted. In some embodiments, the primary gear body 605 diameter may be one inch and/or alternatively may range between 0.5 inches and/or 1.5 inches. In some embodiments, the primary gear body 605 may have a length of 3.5 inches, or alternative may range between 2.75 inches and 8.5 inches. In some embodiments, the diameter of the primary gear assembly may be associated and/or determined by the motor assembly rpm. In this embodiment, the higher the motor assembly rpm the smaller the diameter of the primary gear body of the primary gear assembly. In some embodiments, the primary gear teeth may be 24 teeth and may be at a diametral pitch of 34 teeth per inch.

Figure 7A:
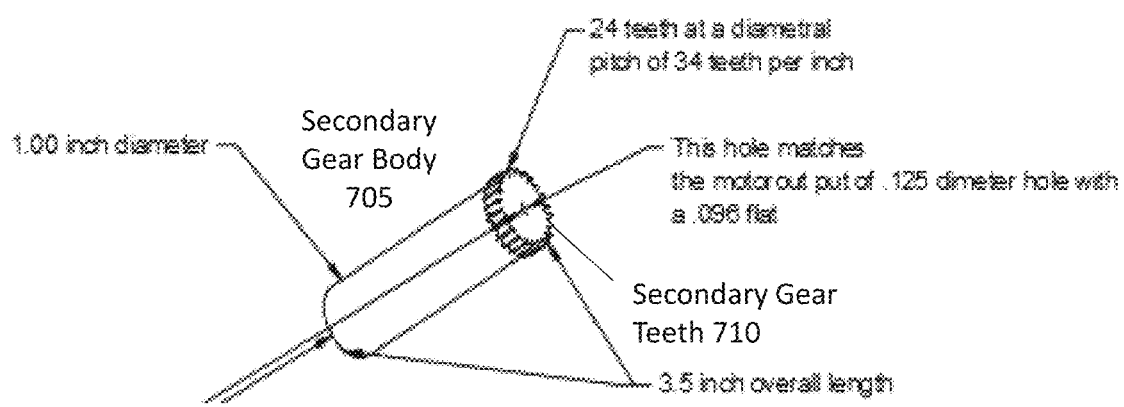
FIG. 7A illustrates a secondary gear assembly according to some embodiments.
Figure 7B:
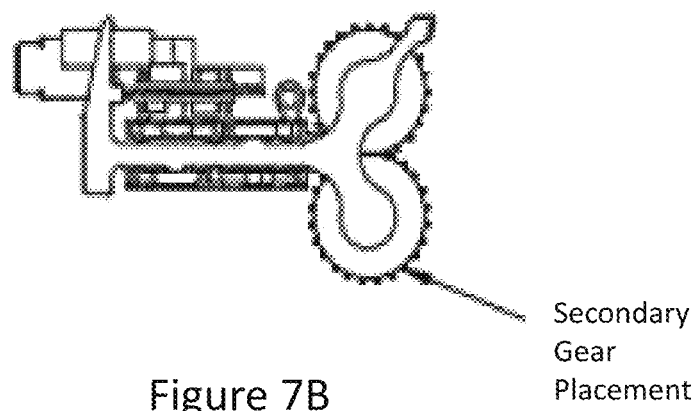
FIG. 7B illustrates a secondary gear placement in a cash sanitizing device according to some embodiments.

FIG. 7A illustrates a secondary gear assembly according to some embodiments. FIG. 7B illustrates a secondary gear placement in a cash sanitizing device according to some embodiments. In some embodiments, the secondary gear includes a secondary gear body 705 and secondary gear teeth 710. In some embodiments, the secondary gear may be the same size and may have the same dimensions as the primary gear. In some embodiments, the secondary gear body may have a one inch diameter, or alternatively may range from 0.35 inches to 1.5 inches. In some embodiments, a smallest bearing of 0.295 may be utilized. In some embodiments, the secondary gear body 705 may have a length of approximately 3.5 inches, or alternatively may range from 2.75 inches to 4.25 inches. In some embodiments, the secondary gear teeth 710 may engage the primary gear teeth 610 when the cash sanitizing device is in operation. In some embodiments, the secondary gear may have 24 secondary gear teeth 710 at a diametral pitch of 34 teeth per inch, although other diametral pitches may be utilized. In some embodiments, the secondary gear placement (shown by reference number 715) is directly below the primary gear so that the cash paper bill exits the cash sanitization device evenly (as is shown in FIG. 7B). In some embodiments, the primary gear and the secondary gear may be of different sizes and a gearing ratio may need to be utilized in order to pull the cash currency through the machine.

Figure 8A:
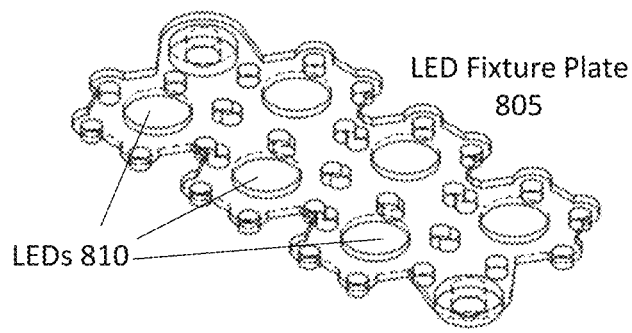
FIG. 8A illustrates a LED fixture plate accordingly to some embodiments.
Figure 8B:
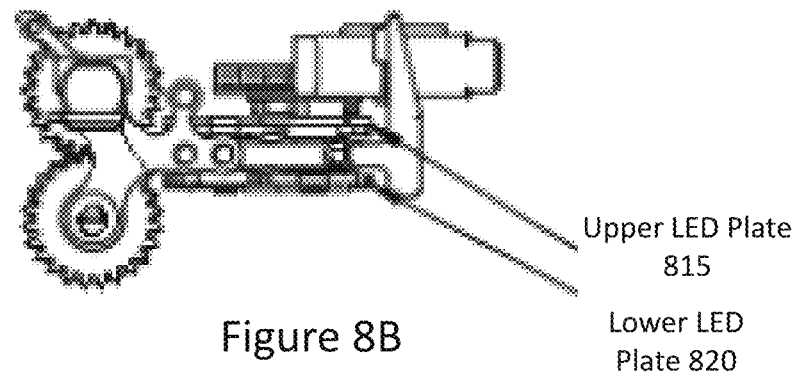
FIG. 8B illustrates placement of the LED fixture plates in the cash sanitizing or sterilizing device according to some embodiments.
Figure 8C:
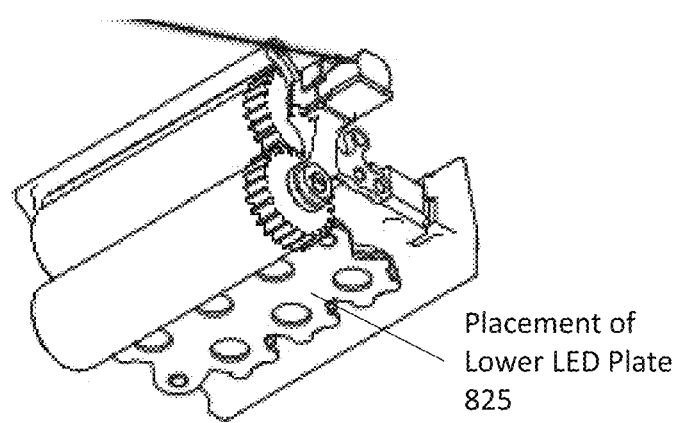
FIG. 8C illustrates a bottom view of placement of the lower LED fixture plate according to some embodiments.

FIG. 8A illustrates a LED fixture plate accordingly to some embodiments. FIG. 8B illustrates placement of the LED fixture plates in the cash sanitizing or sterilizing device according to some embodiments. FIG. 8C illustrates a bottom view of placement of the lower LED fixture plate according to some embodiments. In some embodiments, the cash sanitizing device may have two LED fixture plates (an upper LED plate 815 and a lower LED plate 820). In some embodiments, the LED fixture plate 805 may have a plurality of UV-C LEDs 810 to sanitize the cash paper bill passing in between the two LED fixture plates. In some embodiments, the cash sanitizing device may have an upper LED plate 815 and a lower LED plate 820 and the cash paper bill(s) may pass between the upper LED plate 815 and the lower LED plate 820. In some embodiments, the upper LED plate 815 and the lower LED plate 820 may be connected at one end to the insertion plate 315 and at the other to the gear and motor mount assembly 305. In some embodiments, the LEDs 810 are positioned on the upper LED plate 815 and the lower LED plate 820 in order to provide entire coverage of the cash paper bill and disinfect the upper and lower surface of the cash paper bill passing through the cash sanitizing device. In some embodiments, the upper LED Plate 815 may be connected to a top surface of the main support plate. In some embodiments, the bottom LED plate 820 may be connected to the bottom surface of the main support plate.

The structure of the LED plates (e.g., LED fixture) is also unique and novel as compared to anything in the art. The system is designed in order to provide maximum exposure of UV-C LED light around to the surfaces of the paper bill. In some embodiments, the UVC-LED lights may be approximately 3.0 cm from the cash paper bill. Alternatively, the distance from the UV-C LEDs and the cash paper bill may range from 0.005 inches to 0.25 inches. In some embodiments, the exposure time for each cash paper bill may be between 1 second to 30 seconds. However, if the distance from the UV-C LEDs is shortened, e.g., 0.005 inches (or between 0.005 inches to 0.25, the time of exposure to the UV-C LEDs may be shortened to approximately 0.05 seconds (or between 0.05 to 30 seconds) in order to eliminate all or most of the pathogens. This is because the time required to eliminate the pathogens may be determined by taking a proportion of the new distance (e.g., in this case 1.5 centimeters) with respect to the 3.0 centimeters, squaring this proportion and then multiplying this by the original timeframe (which was 30 seconds. In some embodiments, there may be twelve LEDs 810 in total, six on each LED plate 815 and 820. In some embodiments, the LEDs may be 6.5 volts 275 nanometer UV-C LEDs. In some embodiments, the LEDs 810 may have a 12 millimeter aluminum strata and/or a 0.3×0.3 millimeter heatsink in order to prevent overheating. In some embodiments, the LEDs 810 may be placed in holes that are 0.4 inches in diameter. In some embodiments, the distance between the LEDs in the upper LED plate 815 and the lower LED plate 820 is approximately 0.14 inches. In some embodiments, the distance between LEDs on an upper row on the LED fixture and LEDs on a lower row on the LED fixture may be 0.005-0.25 inches. In some embodiments, the LEDs in the upper LED plate 815 and the lower LED plate 820 are placed about 0.14 inches from the cash paper bill in order to optimally disinfect and/or clean the paper bill from viruses, bacteria and/or germs. In some embodiments, the LED fixture plate may be 2.89 inches in length and 1.39 inches in width, or alternatively may range from 1.5 to 3.2 inches in length and/or 0.8 to 1.8 inches in width.

Figure 9A:
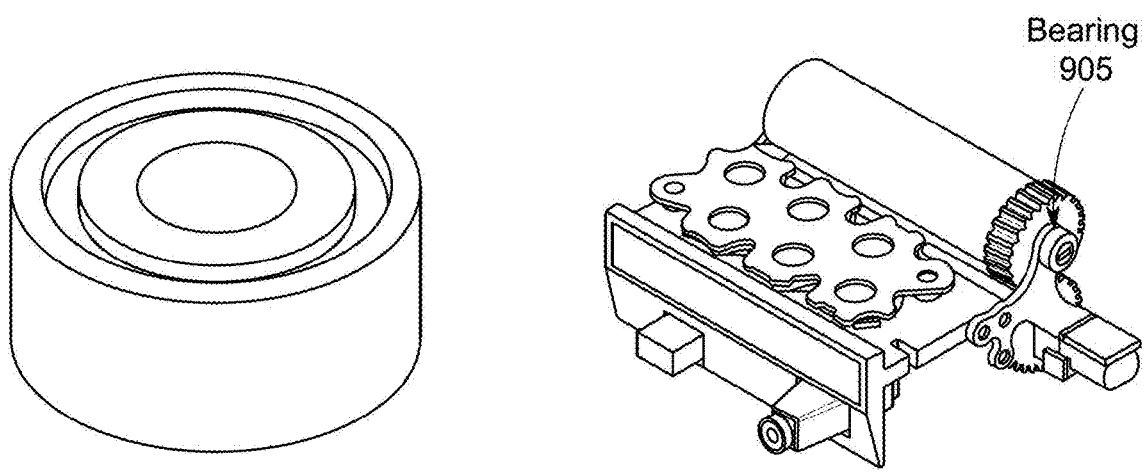
FIG. 9A illustrates a bearing according to some embodiments.
Figure 9B:
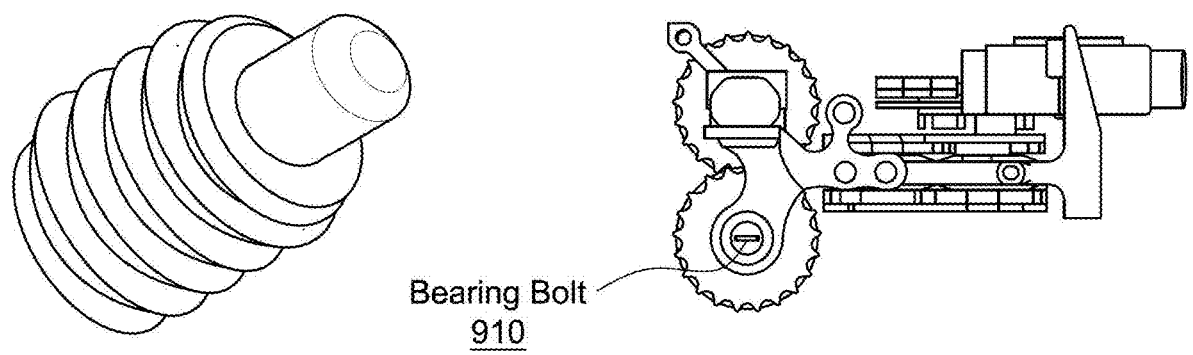
FIG. 9B illustrates a bearing bolt according to some embodiments.

FIG. 9A illustrates a bearing according to some embodiments. In some embodiments, the cash sanitizing device 100 may include three bearings 905. In some embodiments, the three bearings 905 may be positioned in between the side assembly motor mount and the secondary gear to allow the secondary gear to turn smoothly. In some embodiments, the three bearings 905 may be deep groove ball bearings. In some embodiments, the three bearings 905 may be carbon steel bearings, or alternatively, chrome steel ball bearings. In some embodiments, the device may include a different number of bearings. FIG. 9B illustrates a bearing bolt according to some embodiments. In some embodiments, the cash sanitizing device 100 may include three bearing bolts 910. In some embodiments, the three bearing bolts 910 may connect the associated bearing 905 to the side mount assembly.

Figure 10A:
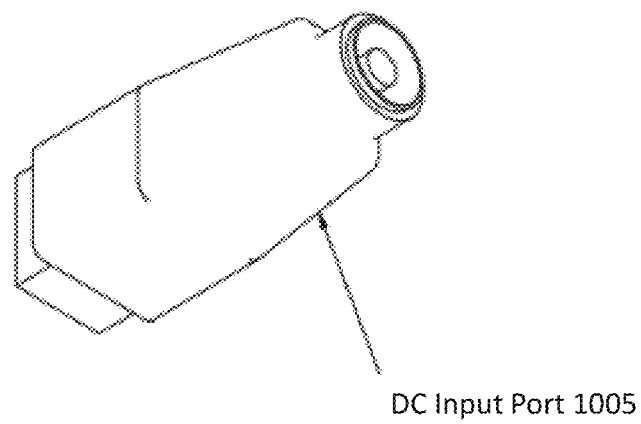
FIG. 10A includes a power input port according to some embodiments.
Figure 10B:
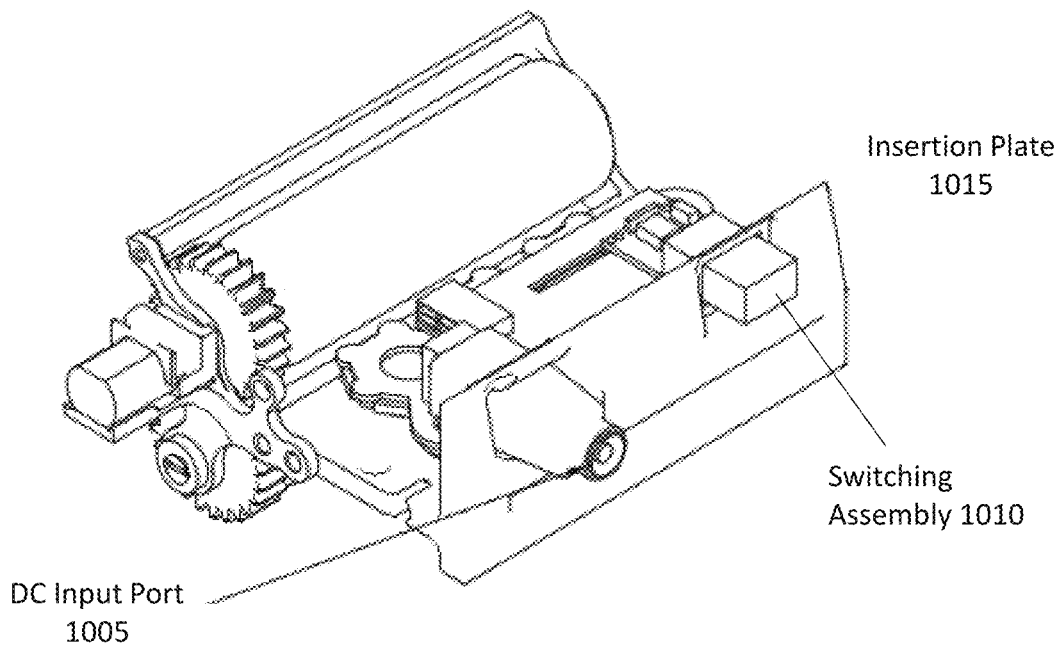
FIG. 10B illustrates a power input port and a switching assembly according to some embodiments.

FIG. 10A includes a power input port according to some embodiments. FIG. 10B illustrates a power input port and a switching assembly according to some embodiments. In some embodiments, the power input port 1005 may be utilized to provide power to the power supplies in the cash dispensing device 100. In the embodiment, the power input port 1005 may be a power input connecter such as is utilized for a laptop computing device. In some embodiments, the power input port 1005 may be a USB-C type of power connector or a mobile communication device (e.g., an iPhone) lightning port type of power connector. In some embodiments, the power input port 1005 may be positioned in an opening of insertion plate to allow access to a power cord. In some embodiments, the switching assembly 1010 may activate turning on and off a cash dispensing device 100. In some embodiments, the switching assembly 1010 may be positioned in an opening of the insertion plate to allow access for a consumer or operator to activate the cash dispensing device.

Figure 10C:
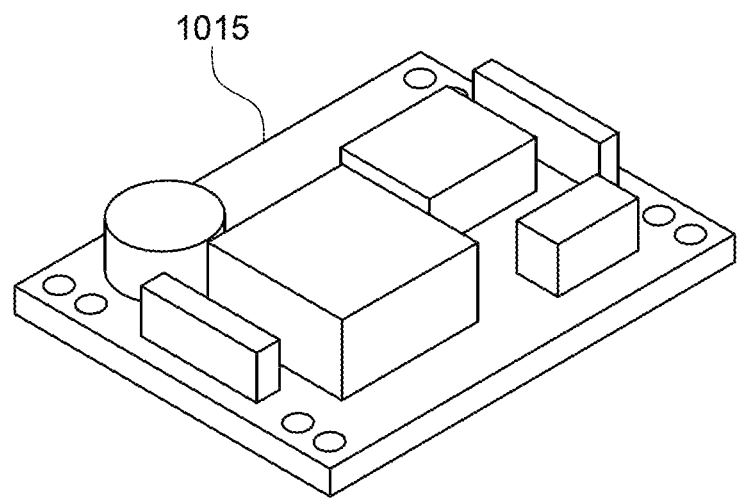
FIG. 10C illustrates a power supply filter and power supplies according to some embodiments.
Figure 10D:
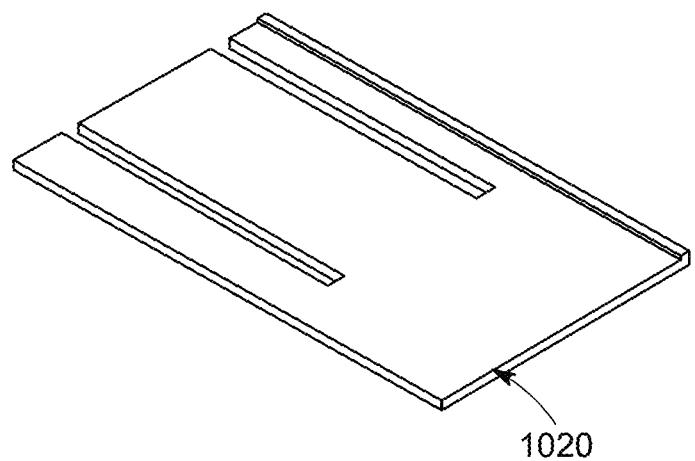
FIG. 10D illustrates an electronics tray according to some embodiments.
Figure 10E:
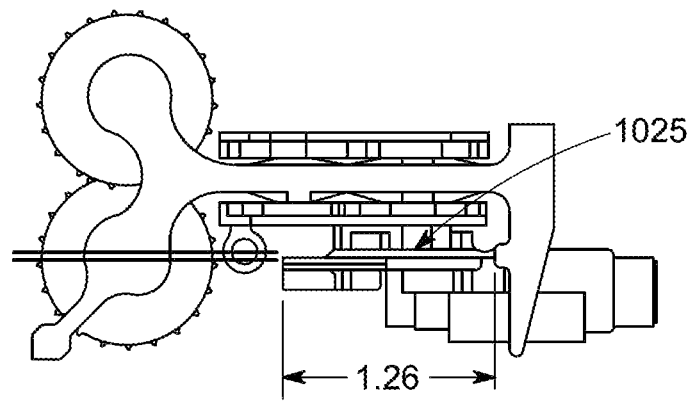
FIG. 10E illustrates positioning of the power supply filter and power supply(s) and the electronics tray in the cash sanitization and/or sterilization device 100.

FIG. 10C illustrates a power supply filter and power supplies according to some embodiments. In some embodiments, the power supply filter and power supply(s) 1015 may receive power from the DC input port 155, filter and/or convert the power and then provide clean and/or filtered DC power to other components of cash sanitizing and sterilizing device 100. In some embodiments, these other components may be the motor assembly and/or the LEDs. In an embodiment, the power supply may covert 24 volts DC power to 3-24 volts DC power. In some embodiments, the power supply and power supply filter may be a DC to DC buck converter. FIG. 10D illustrates an electronics tray according to some embodiments. In some embodiments, the power supply and power supply filter may sit in, be attached to or be positioned in an electronics tray 1020. FIG. 10E illustrates positioning of the power supply filter and power supply(s) and the electronics tray in the cash sanitization and/or sterilization device 100. The positioning and location is shown by reference number 1025.

Figure 11A:
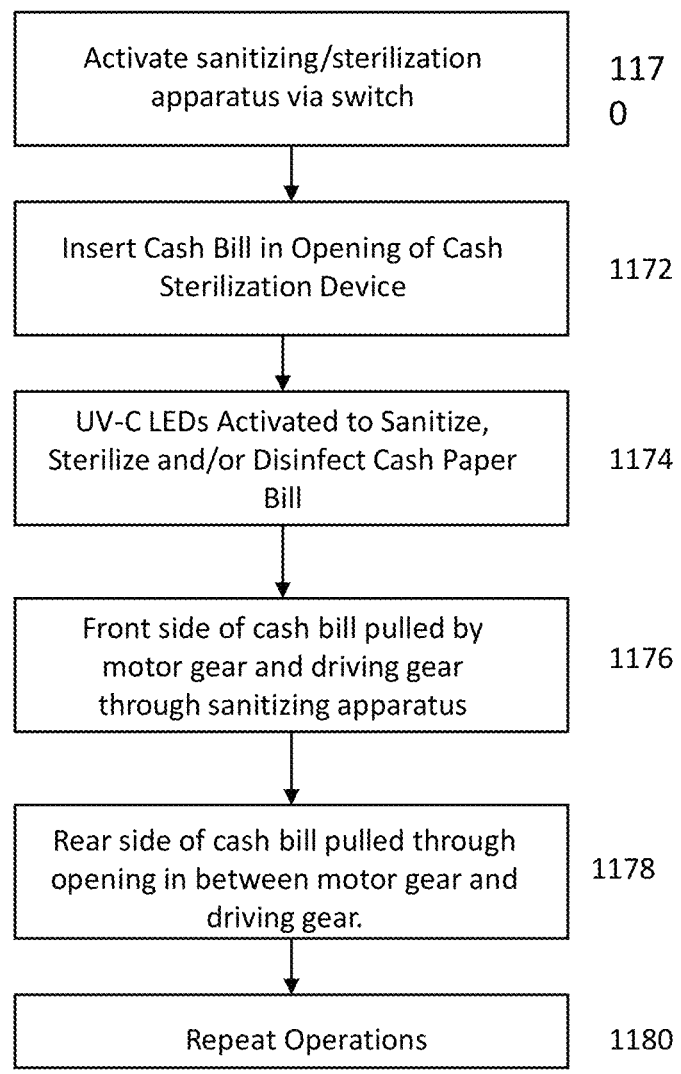
FIG. 11A illustrates a flowchart of operation of a cash paper bill sanitization device according to some embodiments.

FIG. 11A illustrates a flowchart of operation of a cash paper bill sanitization device according to some embodiments. Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step. In some embodiments, in step 1170, a switch or other entry sensor may activate the cash paper bill sanitization device. In some embodiments, in step 1172, a cash paper bill 1105 may be inserted into an opening 1110 of the cash sterilization device. In some embodiments, a thermoresistor or another sensor may sense the presence of the cash paper bill. In some embodiments, the sensing by the thermoresistor or other sensor of the cash paper bill may turn on and/or activate the plurality of UV-C LEDs. In some embodiments, in step 1174, a plurality of UV-C LEDs may be activated and/or turned on to sanitize, sterilize and/or disinfect the inserted cash paper bill. In some embodiments, in step 1176, the primary or motor gear may be engaged (which engages the secondary or driving gear) and a front side of the cash bill is pulled by the motor gear and the driving gear through the cash paper bill sanitization apparatus. In some embodiments, in step 1178, the rear side of the cash paper bill is pulled through the opening in between the motor gear and the driving gear. In some embodiments, in step 1180, the steps 172 through 178 are repeated for any cash paper bill pulled inserted into the opening in the insertion guide motor mount after the original or initial cash paper bill. In some embodiments, the cash paper bill may be fed through the opening in the cash or card sterilization device to the gears and the gears may pull the cash paper bill through the device and it may exit through the exit assembly opening or plate of the cash paper bill sanitization apparatus.

Figure 11B:
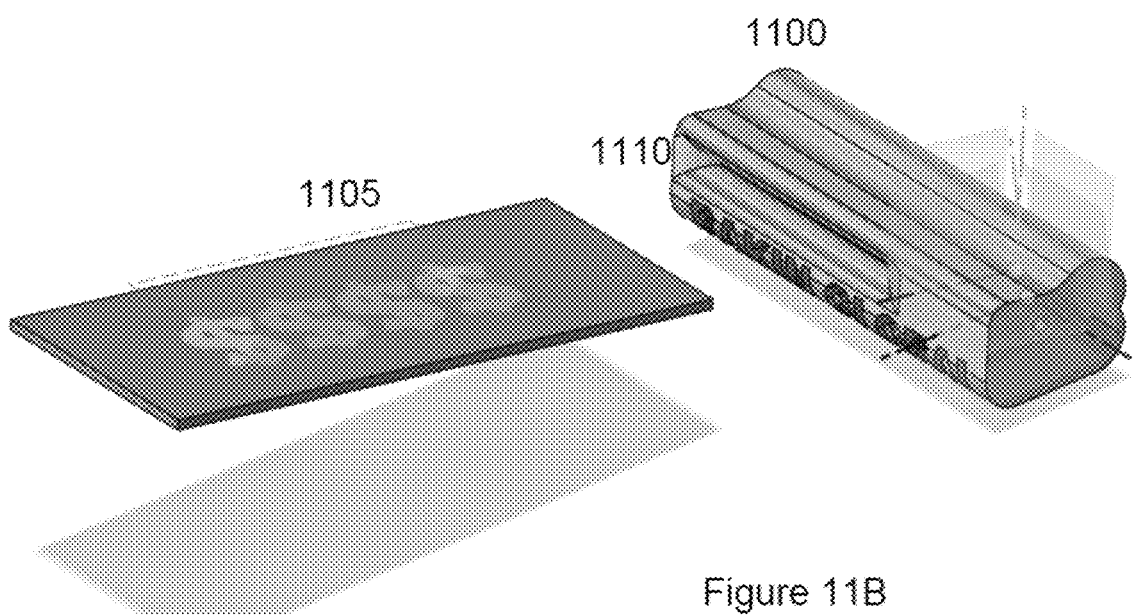
FIG. 11B illustrates the cash paper bill before it is being inserted into the cash sterilization device according to some embodiments.
Figure 11C:
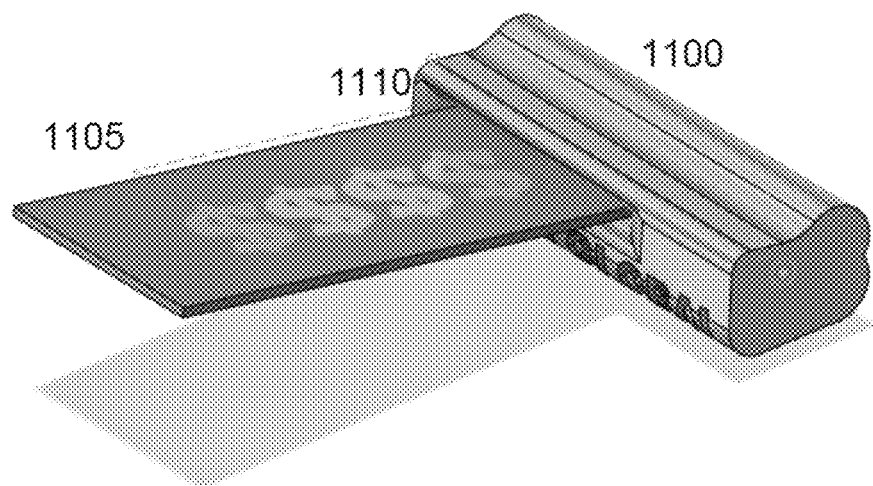
FIG. 11C illustrates the cash paper bill being inserted into the cash sanitization or sterilization device in an insertion opening or insertion plate according to some embodiments.
Figure 11D:
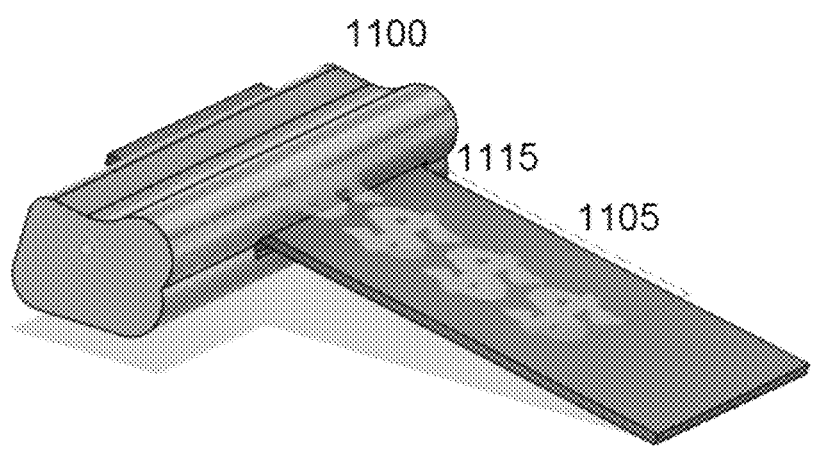
FIG. 11D illustrates the cash paper bill progressing through the insertion plate.
Figure 11E:
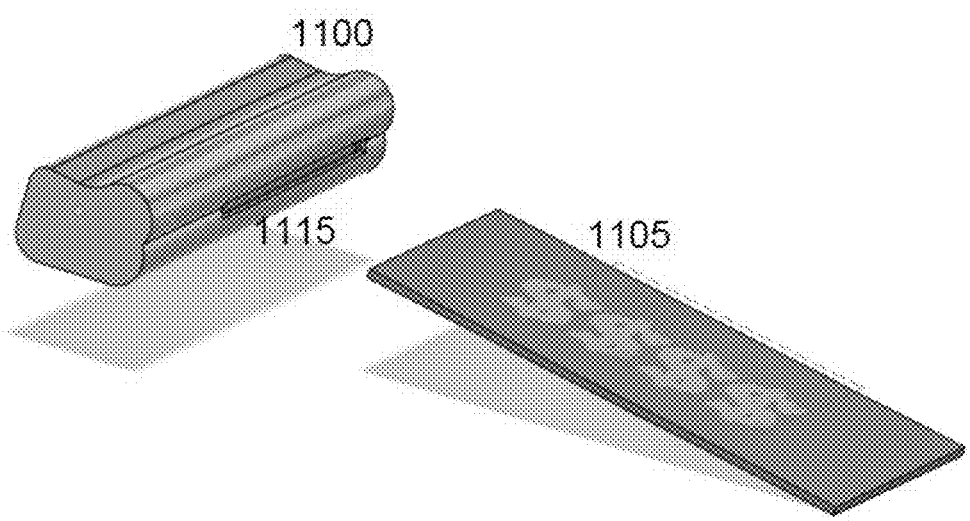
FIG. 11E illustrates when the entire cash paper bill exits the cash sanitization device.

FIGS. 11B-11E illustrate the movement of the cash paper bill 1105 through a cash sanitization device. FIG. 11B illustrates the cash paper bill 1105 before it is being inserted into the cash sterilization device 1100. FIG. 11C illustrates the cash paper bill being inserted into the cash sanitization or sterilization device 1100 in an insertion opening or insertion plate 1110. FIG. 11D illustrates the cash paper bill 1105 progressing through the insertion plate 1100, having a portion of the cash paper bill being irradiated by the UV-C LEDs, and exiting an opening 1115 between the primary roller and secondary roller of the cash sanitization device 1100. FIG. 11E illustrates when the entire cash paper bill 1105 exits the cash sanitization device 1110. The cash sanitation and/or sterilization device 1100 illustrate in FIGS. 11B-11E has an extremely small footprint allowing it to be integrated easily in many other devices such as ATMs and/or other cash dispensing devices (e.g., checkout machines at supermarkets and/or retail superstores (e.g., Walmart and/or Target)).

In some embodiments, the height of the cash paper bill sanitization or sterilization device 1100 may be 1.7 inches or may range from 0.5 inches to 3.0 inches. In some embodiments, the cash sanitization device may have a height of 2.108 inches, a depth of 3.132 inches and/or a width of 4.7491 inches.

Figure 12A:
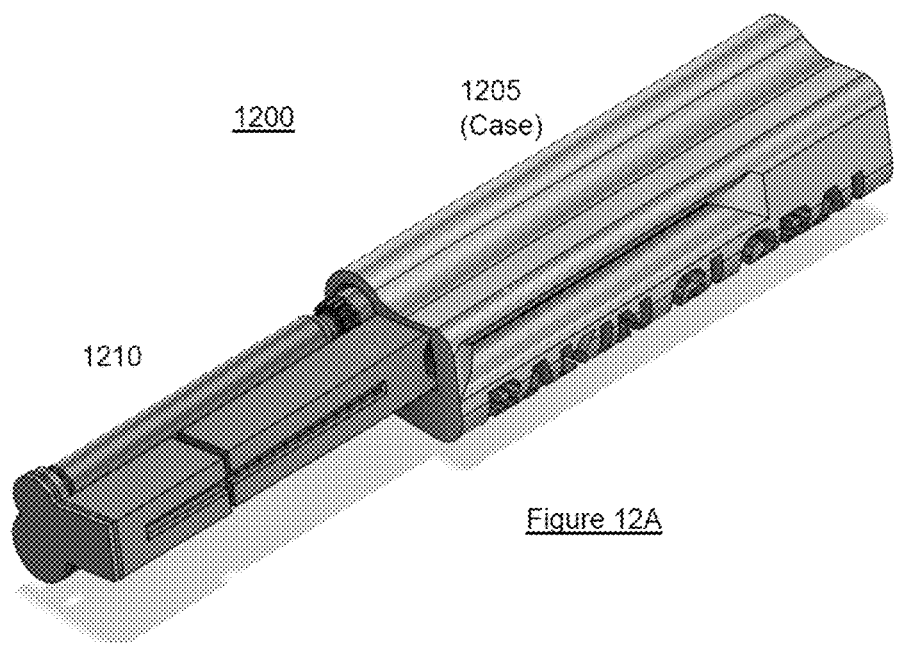
FIG. 12A illustrates a front perspective view of an internal sterilization assembly and a cover assembly or case according to some implementations.
Figure 12B:
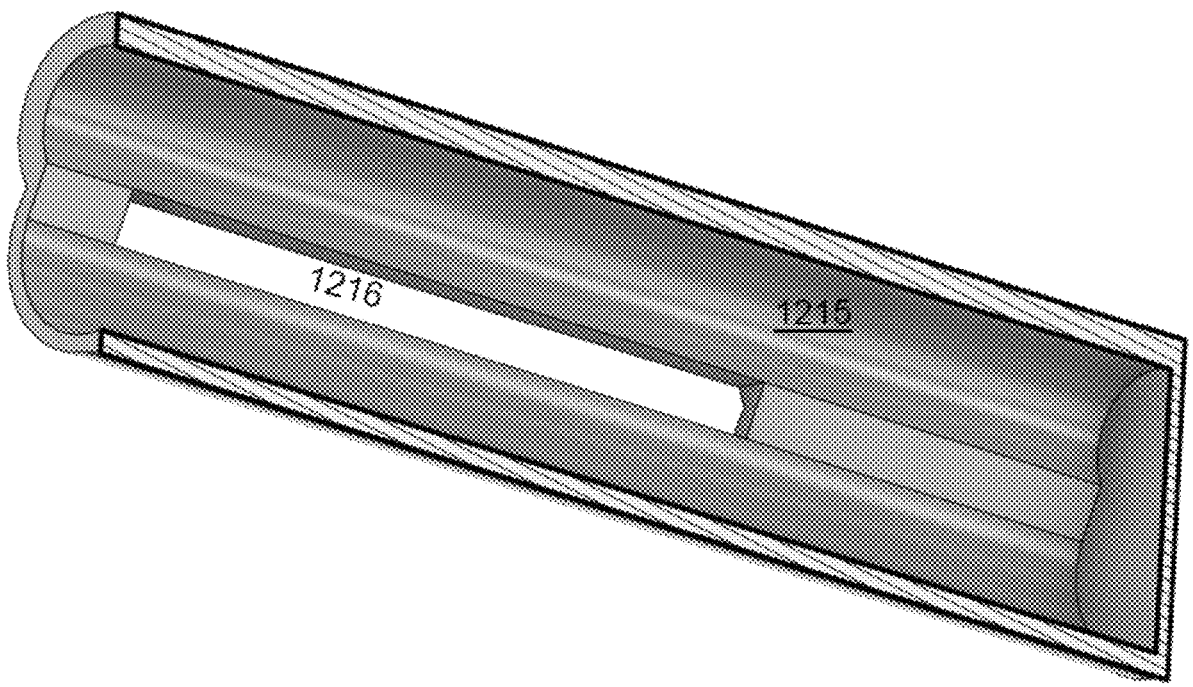
FIG. 12B illustrates an internal view of a back of the cover assembly or case according to some embodiments.
Figure 12C:
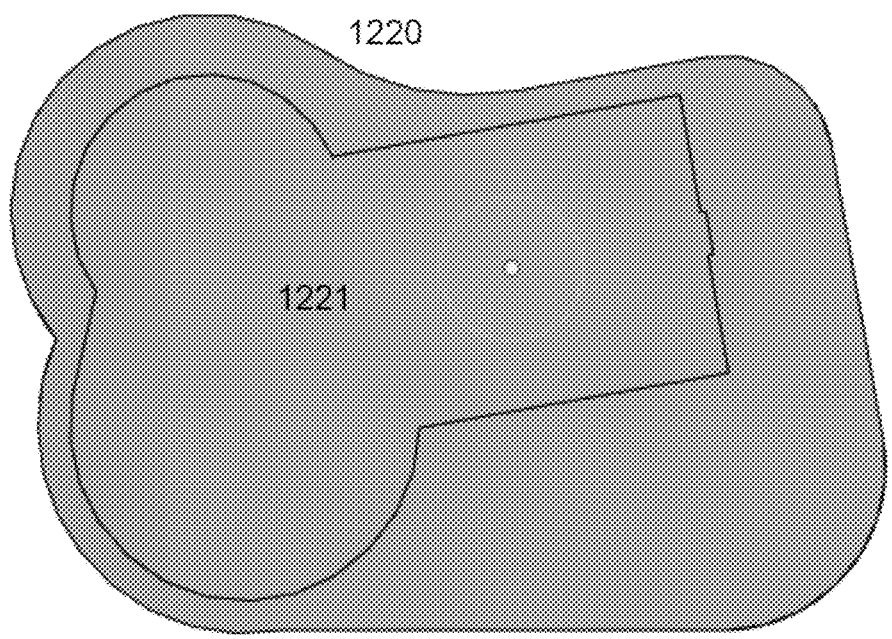
FIG. 12C illustrates an internal view of a side of the cover assembly or case according to some embodiments.
Figure 12D:
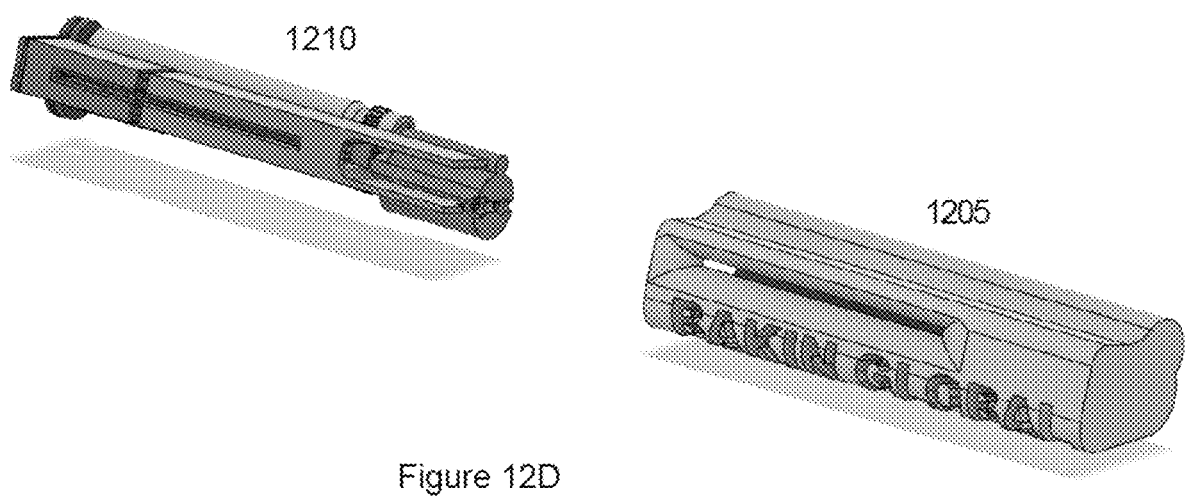
FIG. 12D illustrates a front perspective view of an internal sterilization device and a cover assembly or case.

FIG. 12A illustrates a front perspective view of an internal sterilization assembly and a cover assembly or case according to some implementations. In FIG. 12A, the cash paper bill sterilization device 1200 may include a cover assembly or case 1205 and/or an internal sterilization assembly 1210. In FIG. 12A, the internal sterilization assembly 1210 may be inserted into a side opening of the cover assembly or case 1205. This allows for easy access and/or replacement in case of upgrading, replacement and/or maintenance of components of the internal sterilization assembly and/or of the whole internal sterilization assembly. FIG. 12B illustrates an internal view of a back of the cover assembly or case according to some embodiments. In FIG. 12B, the internal view of the back of the cover assembly 1215 includes an opening 1216 where the cash paper bill may exit the cash sterilization device 1200. FIG. 12C illustrates an internal view of a side of the cover assembly or case according to some embodiments. In FIG. 12C, the cover assembly or case includes a side or end 1120 and the internal side or end 1220 includes an area 1221 on which an end of the internal sterilization device contacts or rests against the side or end 1220 cover assembly or case. FIG. 12D illustrates a front perspective view of an internal sterilization device and a cover assembly or case. In FIG. 12D, the internal sterilization device 1210 is completely separated from the cover assembly or case 1205.

Figure 13A:
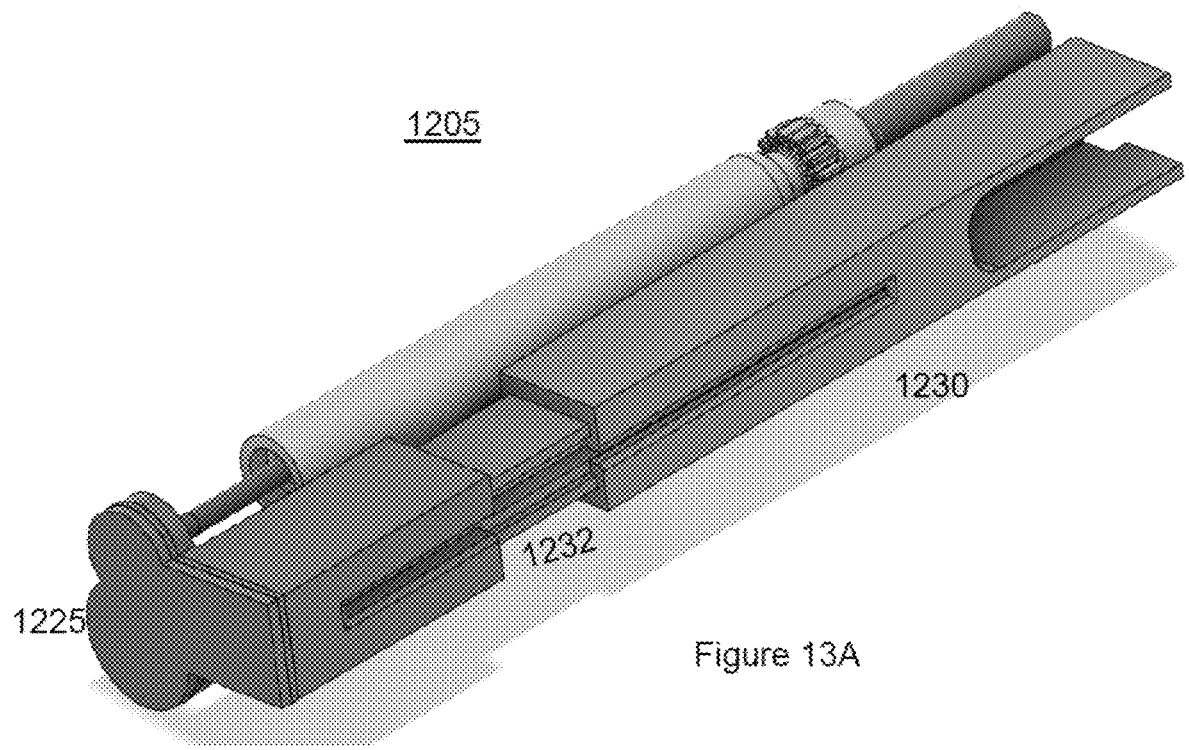
FIG. 13A illustrates a front perspective view of an internal sterilization assembly or component according to some embodiments.
Figure 13B:
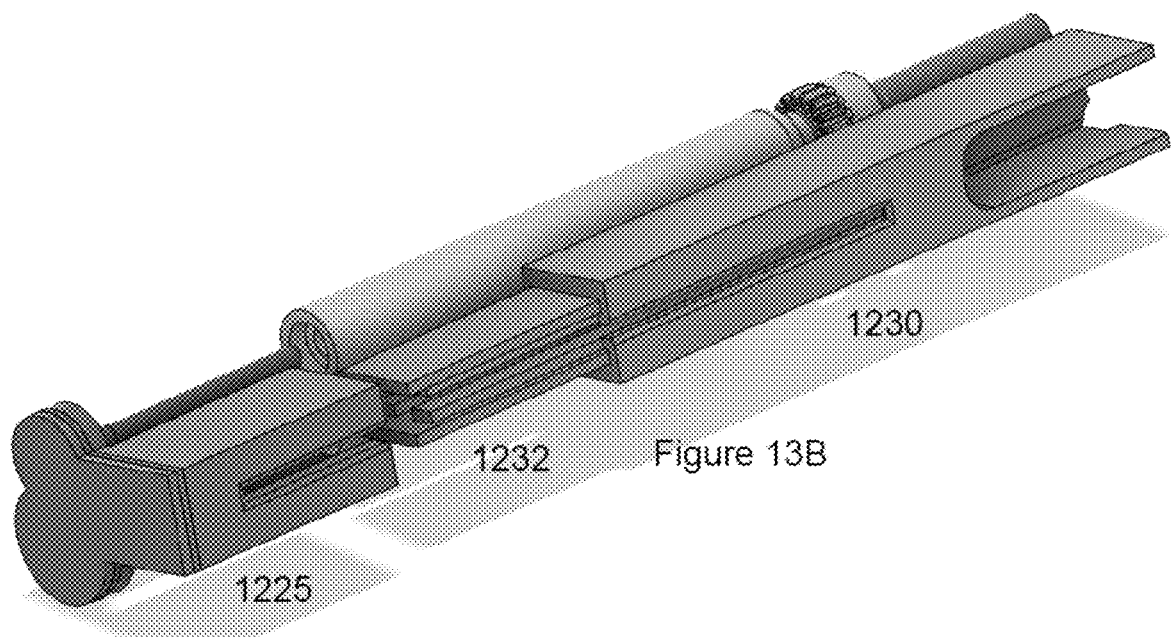
FIG. 13B also illustrates a front perspective view of the internal sterilization assembly or component according to some embodiments.
Figure 13C:
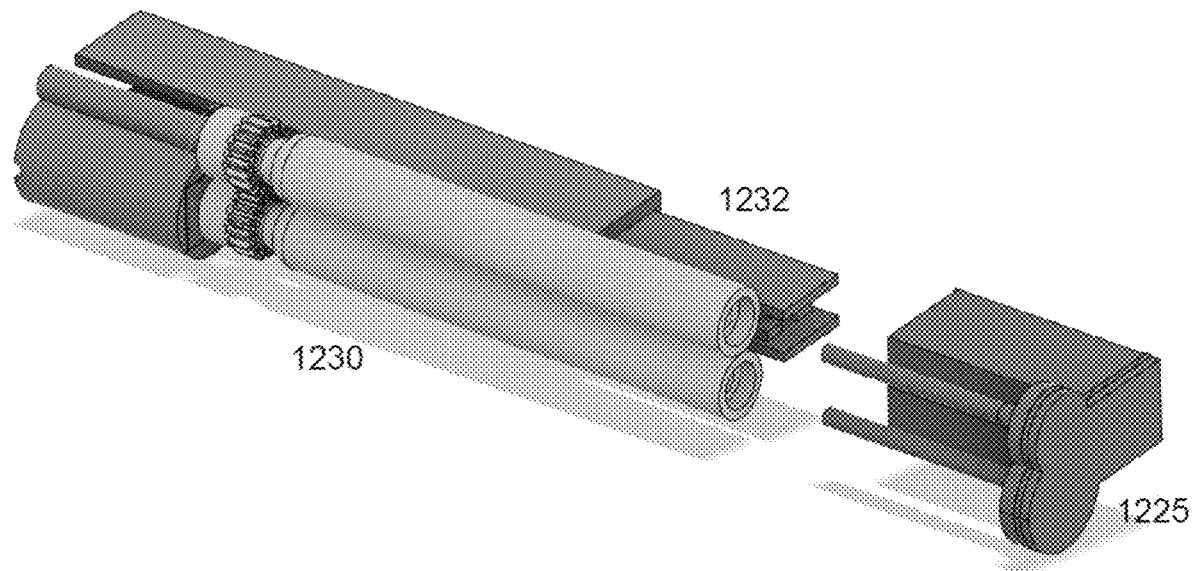
FIG. 13C illustrates a back view perspective of the internal sterilization assembly or component according to some embodiments

FIG. 13A illustrates a front perspective view of an internal sterilization assembly or component according to some embodiments. FIG. 13B also illustrates a front perspective view of the internal sterilization assembly or component according to some embodiments. FIG. 13C inserts a back view perspective of the internal sterilization assembly or component according to some embodiments. In some embodiments, the internal sterilization assembly or component 1205 may comprise a cap assembly 1225 and a sterilization assembly/component main body 1230. In these embodiments, the sterilization assembly/component main body 1230 may be inserted into the cap assembly or housing 1225 and/or the internal sterilization assembly 1210 may be inserted into the cover assembly or case 1205. In some embodiments, the LED assembly 1232 may be inserted into an opening of the internal sterilization main body 1230. In some implementations, the LED assembly 1232 may be modular and may be able to be replaced easily, as compared to other modules that are not easily replaceable. In these embodiments, one end of the LED assembly 1232 may be inserted into the cap assembly 1225 and an opposite end of the LED assembly 1232 may be inserted into an opening of the internal sterilization assembly main body 1230

Figure 13D:
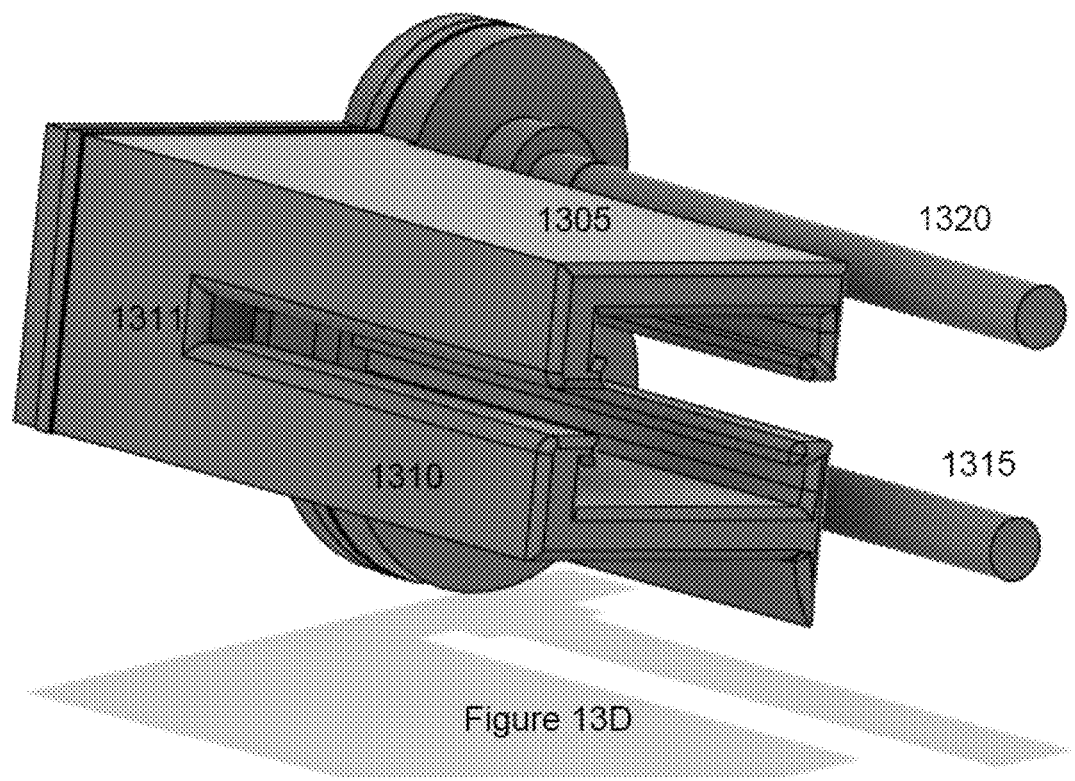
FIG. 13D illustrates a front view of a cap assembly or housing according to some embodiments.

FIG. 13D illustrates a front view of a cap assembly or housing according to some embodiments. In some embodiments, the cap assembly or housing includes a top LED guide 1305, a bottom LED guide 1310, a first portion of a paper bill opening 1311, one or more motor gear roller assembly guides 1315 and/or one or more driving gear roller assembly guides 1320. In some embodiments a top LED assembly may be placed into the top LED guide 1305 and a bottom LED assembly may be placed into the bottom LED guide 1310. In some embodiments, an end of the motor gear roller assembly may be inserted onto or around the one or more motor gear guides 1315. In some embodiments, an end of a driving gear roller assembly may be inserted onto or around the one or more driving gear guides 1320.

Figure 13E:
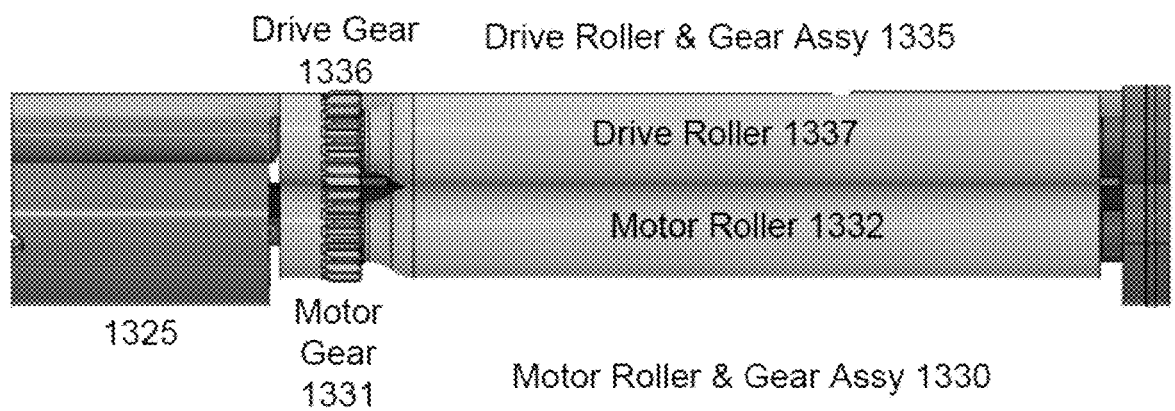
FIG. 13E illustrates a back view of an internal sterilization assembly or components according to some embodiments.

FIG. 13E illustrates a back view of an internal sterilization assembly or components according to some embodiments. In some embodiments, the internal sterilization assembly or component 1310 may include one or more motors or motor assemblies 1325, one or more motor roller gear assemblies 1330, and/or one or more driving roller gear assemblies 1335. In some embodiments, the one or more motor roller gear assemblies 1330 may include one or more motor gears 1331 and/or one or more motor rollers 1332. In some embodiments, the one or more driving gear assemblies 1335 may include one or more driving gears 1336 and/or one or more driving rollers 1337. In some embodiments, the one or more motors 1325 may be turned on or activated (e.g., by a motor controller) and may turn or rotate one or more motor shafts. In some embodiments, the one or more motor roller gear assemblies 1330 may be located below or above (or directly below or above) the driving roller gear assemblies 1335. In some embodiments, the one or more motor shafts may rotate the one or more motor rollers 1332 and/or the one or more motor gears 1331. In some embodiments, the one or more motor gears 1331 may be engaged and/or aligned with the one or more driving gears 1336. In these embodiments, the rotations of the one or more motor gears 1331 causes rotation of the one or more driving gears 1336. In some embodiments, the rotation of the one or more driving gears 1336 causes rotation of the one or more driving rollers 1337. In these embodiments, the rotation of the rotation of the one or more driving rollers 1337 causes any cash bill which is placed and/or positioned in between the motor roller 1332 and the driving roller 1337 to move through the internal sterilization assembly or component 1310. In some embodiments, the cash bill or cash paper bill may be replaced by a debit card, a credit card, and/or a gift card.

Figure 13F:
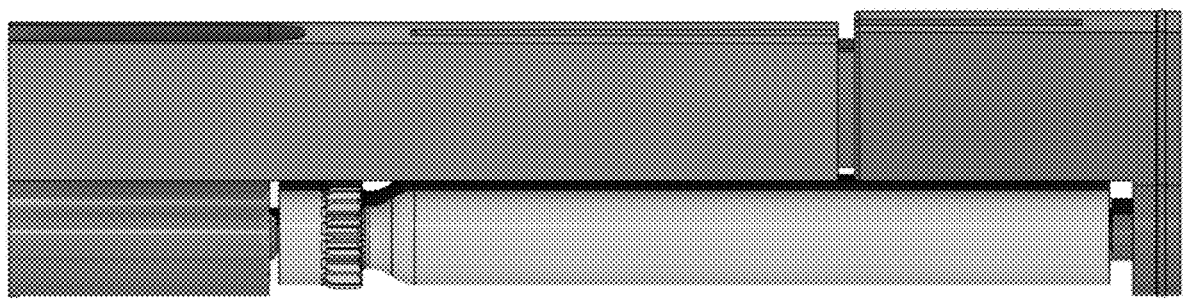
FIG. 13F illustrates a top view of an internal sterilization assembly or component inserted into the case or cover assembly according to some embodiments.
Figure 13G:
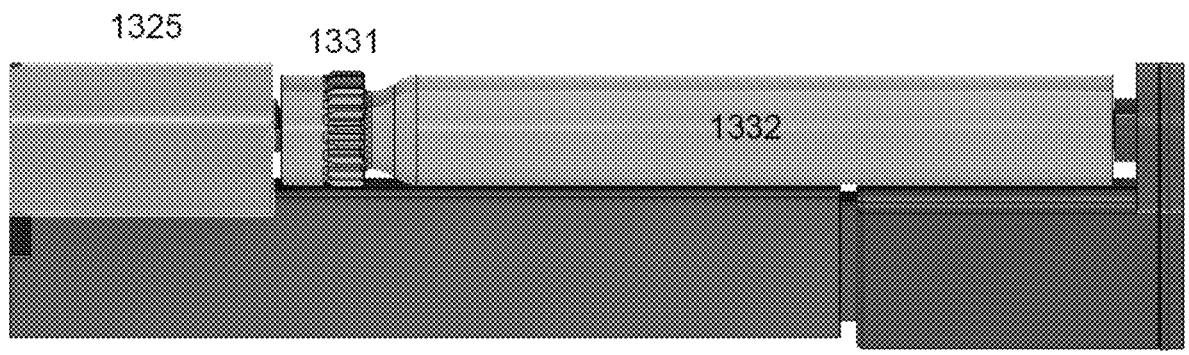
FIG. 13G illustrates a bottom view of the internal sterilization assembly or component inserted into the case or cover assembly according to some embodiments.

FIG. 13F illustrates a top view of an internal sterilization assembly or component inserted into the case or cover assembly 1225 according to some embodiments. FIG. 13F illustrates a clear view of the motor gear roller assembly 1330 according to some embodiments. FIG. 13G illustrates a bottom view of the internal sterilization assembly or component inserted into the case or cover assembly according to some embodiments. FIG. 13G illustrates a clear view of the motor assembly 1325 connected to the motor roller gear assembly 1330. FIG. 13E illustrates the motor gear roller assembly 1330 and the driving gear roller assembly 1335. More specifically, the motor assembly 1325 rotates a motor shaft which may be coupled to the motor gear 1331 and rotates the motor gear 1331. In some embodiments, the motor roller or roller assembly 1332 may rotate the motor gear 1331. In some embodiments, the motor gear 1331 may be engaged with the driving gear 1336 and thus may rotate the driving gear 1336. In these embodiments, the rotation of the driving gear 1336 may cause the driving roller or roller assembly 1337 to rotate and pull the cash paper bill through the cash paper bill sterilization device.

Figure 13H:
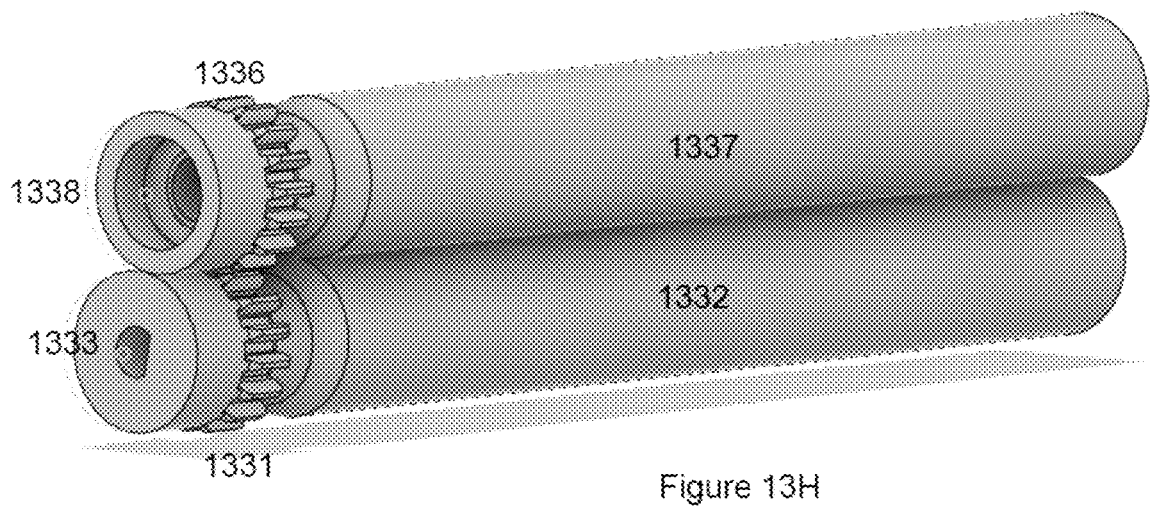
FIG. 13H illustrates an isometric view of the motor gear assembly and the driving gear assembly.
Figure 14A:
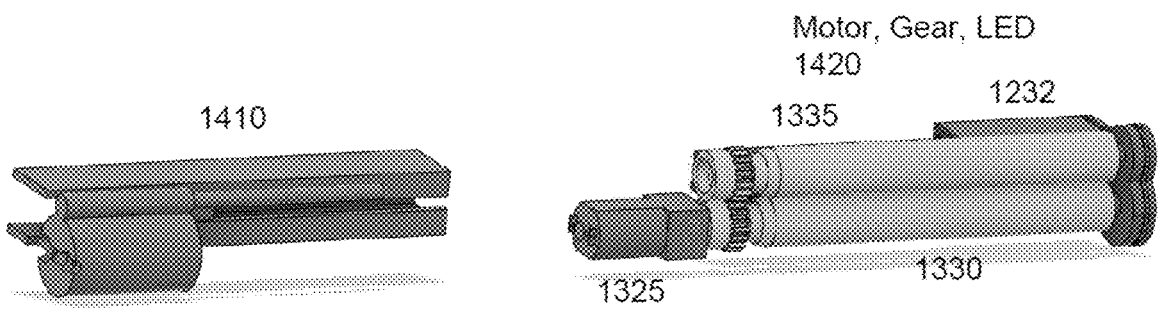
FIG. 14A illustrates a LED and motor case or cover and a motor, gear and LED assembly according to some embodiments.
Figure 14B:
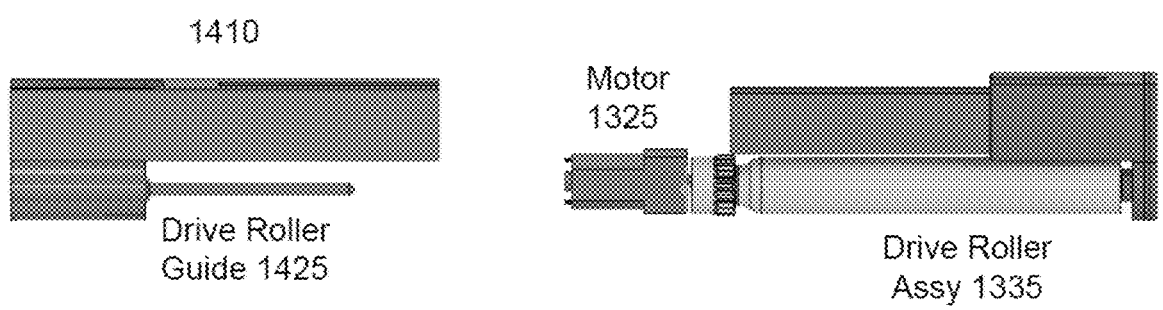
FIG. 14B illustrates a top view of a LED and motor case or cover and a motor, gear and LED assembly according to dome embodiments.

FIG. 13H illustrates an isometric view of the motor gear assembly and the driving gear assembly. In FIG. 13H, the driving roller gear assembly 1335 may be located directly above and aligned with the motor roller near assembly 1330. In these embodiments, the motor roller gear assembly 1330 includes a shaft opening or hole 1333, a motor gear 1331 and/or a motor rollers 1332. In these embodiments, the motor shaft of the motor assembly 1325 may be inserted into the shaft opening or hole 1333. In some embodiments, driving roller gear assembly 1135 may include a drive opening or hole 1338, a drive gear 1336, and/or a drive roller 1337. In some embodiments, a driving roller guide may be positioned in the driving opening or hole 1338 to keep the driving roller gear assembly in place FIG. 14A illustrates a LED and motor case or cover and a motor, gear and LED assembly according to some embodiments. FIG. 14A illustrates a rear view. In FIG. 14A, in some embodiments, the internal sterilization assembly includes an LED and motor case or cover 1410 and a motor, gear and LED assembly 1420. In some embodiments, the motor, gear and LED assembly 1420 is inserted into and/or position into the LED and motor case or cover 1410. The motor gear and LED assembly 1420 may include one or more motor assemblies 1325, the motor roller gear assembly 1330, the driving roller gear assembly 1335 and/or the LED assembly 1232. When looking at the cash paper bill sterilization device, the LED assembly 1232 is in front of the motor roller gear assembly 1330 and the driving roller gear assembly 1335. In these embodiments, the opening in the LED assembly 1232 (which is between two LED plates) is aligned with an opening between the motor roller gear assembly 1330 and the driving roller gear assembly 1335. FIG. 14B illustrates a top view of a LED and motor case or cover and a motor, gear and LED assembly according to some embodiments. In FIG. 14B, the additional component of the LED and motor case or cover 1410 is the driving gear assembly support or guide 1425. In some embodiments, the driving gear assembly support or guide 1425 may be inserted into an opening or hole 1338 of the driving roller gear assembly 1335 in order to maintain the place of the driving roller gear assembly 1335.

Figure 15A:
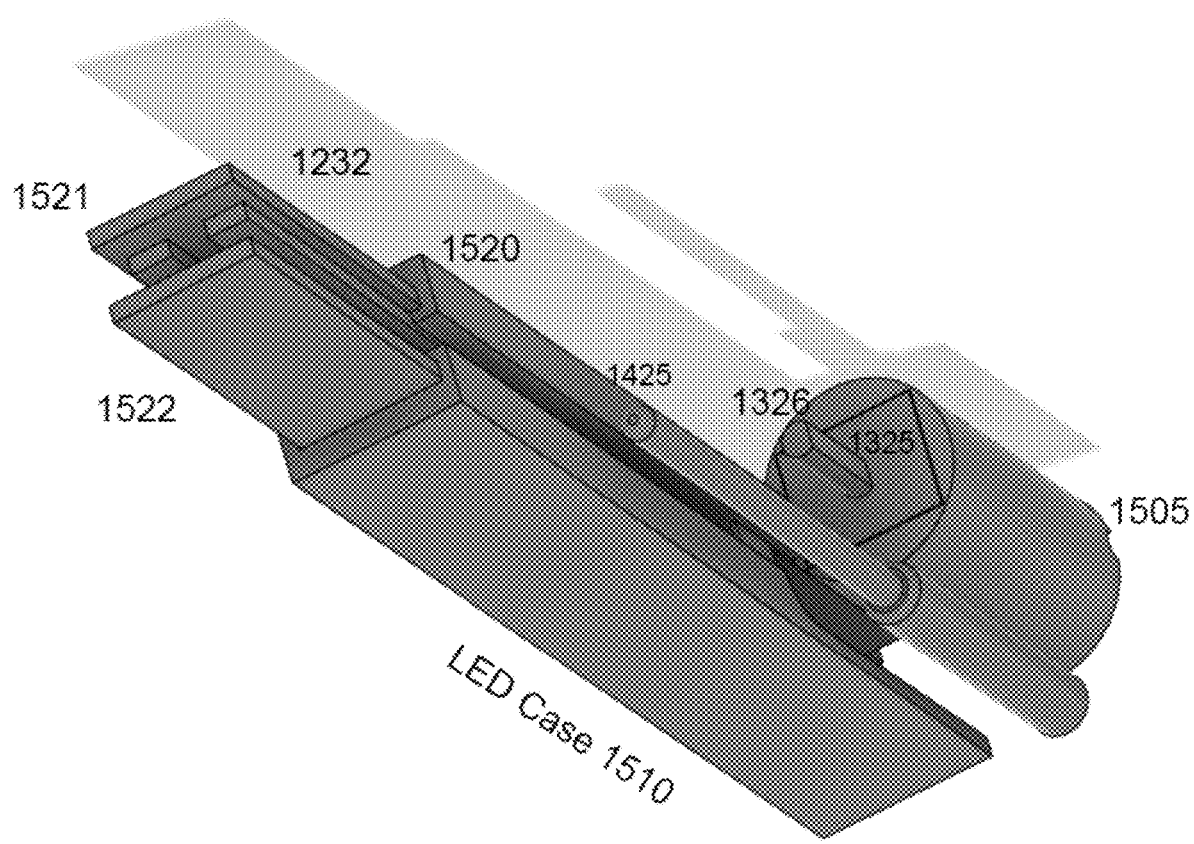
FIG. 15A illustrates a back view of the LED and motor casing with the LED assembly and the motor inserted according to some embodiments.

FIG. 15A illustrates a back view of the LED and motor casing or cover with the LED assembly and the motor or motor assembly inserted according to some embodiments. In some embodiments, the motor assembly 1325 may be inserted into the opening in the motor assembly case or cover 1505. In some embodiments, the motor assembly 1325 may be square or may be rectangular in shape and may be fit into a square or rectangular opening of the motor assembly case 1505. In some embodiments, the motor shaft 1326 may be attached to the motor assembly 1325. In some embodiments, the LED case 1510 may include a top portion 1515 (which may be rectangular in shape) and a bottom portion 1520 (which may be rectangular in shape). Other shapes may be utilized based on the design of the LED assemblies. In these embodiments, a top LED plate or printed circuit board (PCB) 1516 may be inserted into the top portion 1515 of the LED case 1510. In these embodiments, a bottom LED plate or PCB 1521 may be inserted into the bottom portion 1520 of the LED case 1510. In some embodiments, the combination of the LED case 1510 and the motor casing or cover 1505 may be referred to as a motor and LED cover. In some embodiments, a top portion 1515 of the LED case 1510 may be referred to as an upper LED cover assembly and the bottom portion 1520 of the LED case 1510 may be referred to as a lower LED cover assembly.

Figure 15B:
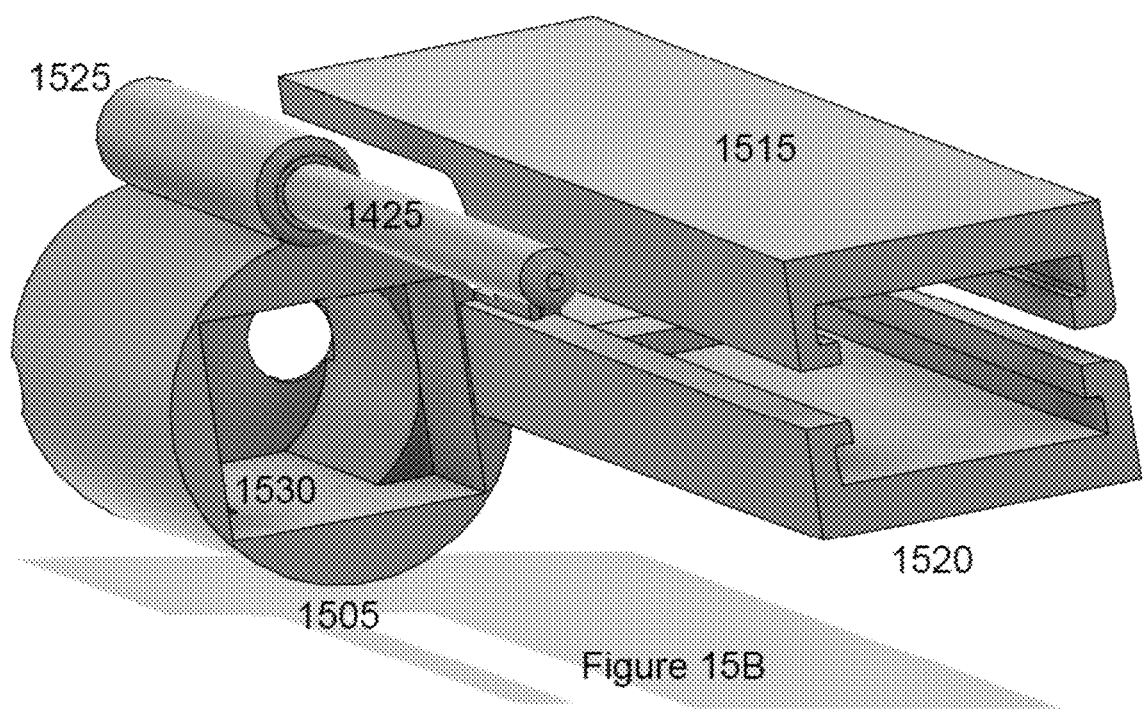
FIG. 15B illustrates a side view of the LED and motor casing according to some embodiments.
Figure 15C:
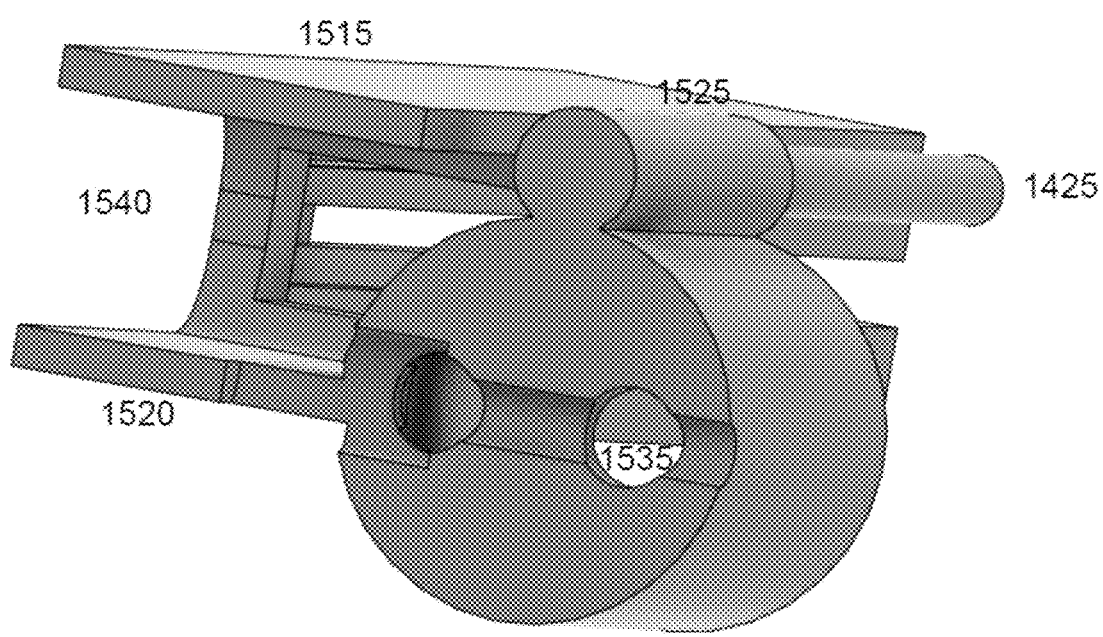
FIG. 15C illustrates a back or rear view of FIG. 15B according to some embodiments.

FIG. 15B illustrates a side view of the LED and motor casing or cover according to some embodiments. In some embodiments, the top portion 1515 of the LED case 1510 may be connected or coupled to the bottom portion 1520 of the LED case 1510. In some embodiments, the driving roller guide 1425 may be coupled to a support post 1525. FIG. 15C illustrates a back or rear view of FIG. 15B according to some embodiments. In some embodiments, the back of the motor casing 1505 may include two wiring openings or holes 1535. In some embodiments, wiring for the motor assembly 1325 and/or wiring for the LED assemblies 1516 and 1521 may pass through the wiring openings or holes 1535. In these embodiments, the wiring may be connected to a power supply which provides power to the cash paper bill sterilization device. In these embodiments, the wiring may be connected to one or more processors or controllers that control operations of the cash paper bill sterilization device including activation of the LED assemblies 1516 and/or 1521 and/or other electro-mechanical components. In some embodiments, the LED and motor casing assembly may also include an open area 1540 where a controller and/or microprocessor and/or other printed circuit board may be placed to provide additional functionality for the cash paper bill sterilization device.

In some embodiments, one or more controllers and/or processors may be located within the cash sterilization device shown in the various figures, outside the cash sterilization device and/or within the open area 1540 described above. In some embodiments, the cash sterilization device may have one or more processors or controllers, one or more memory devices, and/or computer-readable instructions stored in the one or more memory devices. These components may be located on a printed circuit board (PCB) or another chip. In some embodiments, the computer-readable instructions may be stored in one or more memory devices, accessible and/or executable by one or more processors to assist to control operations of the cash sterilization device. In these embodiments, for example, the cash sterilization device may include different color lighting assemblies. In these embodiments, different color lights may be utilized to show different operation states of the cash sterilization device. For example, green lights may indicate that the device is operating and sterilizing bills or cards; yellow lights may indicate that the device is done sterilizing or completed sterilizing bills or cards; red lights may indicate that the sterilization device is an error state. In some embodiments, other light colors may also be utilized. In some embodiments, the computer-readable instructions may be executable by the one or more processors to assist the cash sterilization device in counting money and/or counting the number of bills or cards that have passed through and/or been sterilized by the sterilization device. In these embodiments, the cash sterilization device may include sensors, and/or cameras that are utilized to sense the bills or cards passing through (and to count a number of the bills or cards passing through and/or processed/sterilized). If money amounts are being counted, then the cash sterilization device's camera may be utilized to capture the cash paper bill amount and/or software may be utilized to perform image processing on the bills or cards. In some embodiments, the cash sterilization device may also include one or more wireless communication transceivers. This may allow external computing devices (e.g., laptops, mobile phones, mobile communication devices, computing devices, wearable computing devices and/or tablets) to control operation of the cash sterilization device.

Figure 15D:
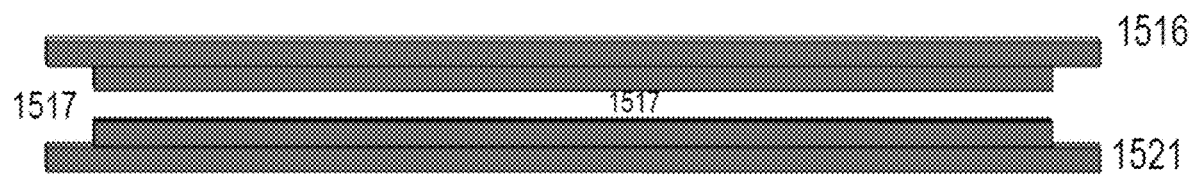
FIG. 15D illustrates a positioning of the top LED plate or PCB with respect to the lower LED plate or PCB.
Figure 15E:
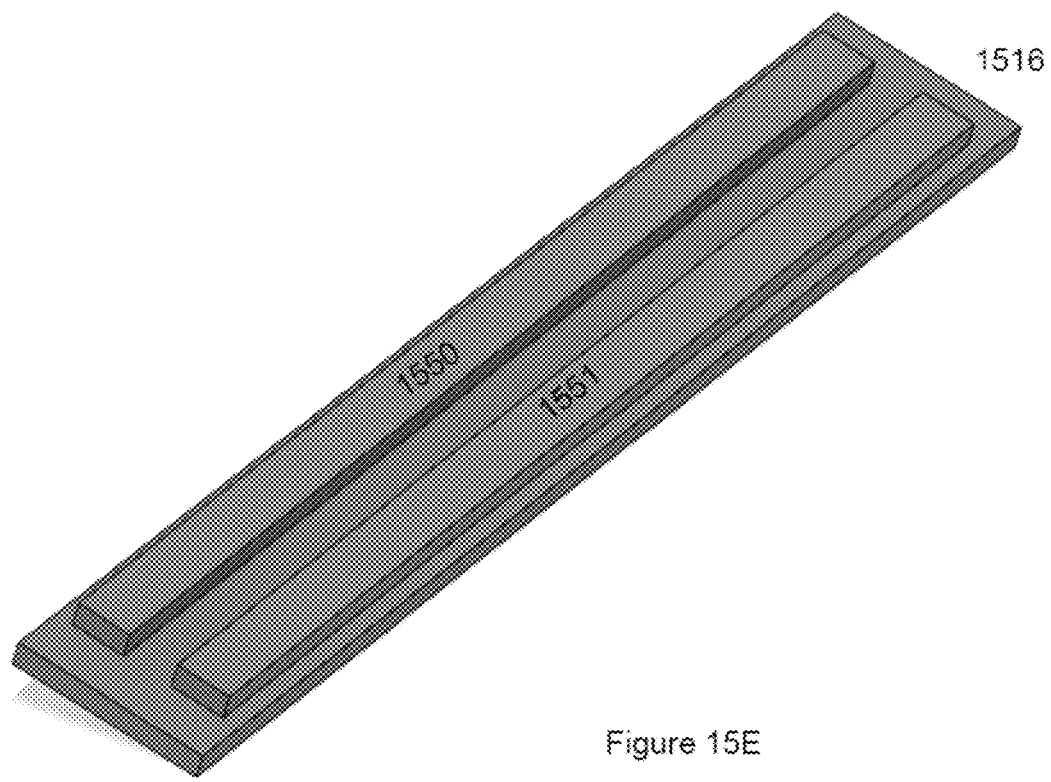
FIG. 15E illustrates alignment of LED strips on an LED plate according to some embodiments.

FIG. 15D illustrates a positioning of the top LED plate or PCB with respect to the lower LED plate or PCB. In these embodiments, the top LED plate or PCB 1516 may be positioned directly above the bottom LED plate or PCB 1521. In these embodiments, the top LED plate, assembly or PCB 1516 may be aligned with the bottom LED plate, assembly or PCB 1521 so there is exact or close to exact alignment (e.g., where there is a LED on the top LED plate, assembly or PCB 1516, there is an LED directly below it (or aligned with it)) on the bottom LED plate, assembly or PCB 1521. FIG. 15D illustrates an opening 1517 between the top LED plate 1516 and the bottom LED plate, assembly or PCB 1521. FIG. 15E illustrates alignment of LED strips on an LED plate according to some embodiments. In these embodiments, the bottom LED plate 1521 includes two LED strips (or plurality of LED assemblies) 1550 and 1551. In the embodiment illustrated in FIG. 15E, the LED strip 1550 is horizontally aligned with the LED strip 1551.

Figure 15F:
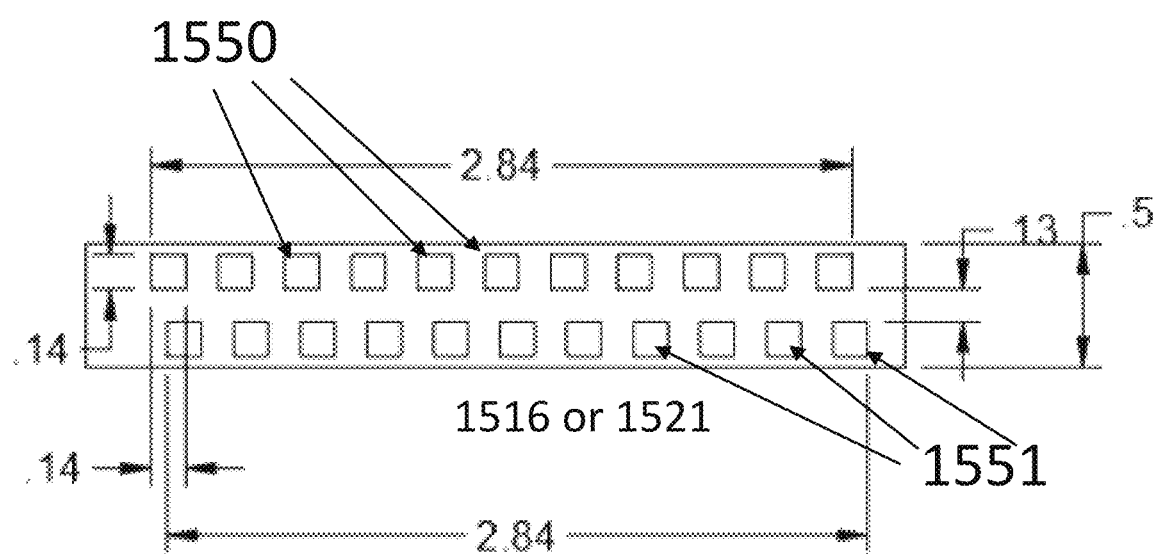
FIG. 15F illustrates an LED assembly or PCB according to some embodiments.

FIG. 15F illustrates an LED assembly or PCB according to some embodiments. The LED assembly, plate or PCB illustrated in FIG. 15F may be either the top LED plate, assembly or PCB 1516 or the bottom LED plate, assembly or PCB 1521. In some embodiments, each LED strip (e.g., LED strips or rows 1551 and/or 1550 may include a plurality of LEDs in order to cover the entire area of the paper cash bill or card passing through the cash or card sterilization device. In FIG. 15F, there are 11 LEDs in each of the LED strips or rows 1550 and 1551. In some embodiments, one LED strip or row 1550 may be directly aligned with the other LED strip or row 1551. In the embodiment illustrated in FIG. 15F, the LED strip or row 1550 is slightly offset from the LED strip or row 1551. In some embodiments, the LEDs may be 0.14 inches or centimeters in length and width, e.g., they may be a square shape, but other shapes may be utilized. In some embodiments, the LEDs may range from 0.05 to 0.25 inches or centimeters in length and/or width. In some embodiments, there may be a space of 0.13 inches or centimeters between the LED strip or row 1550 and the LED strip or row 1551. In some embodiments, there may be a space ranting from 0.05 to 0.25 between the LED strip or row 1550 and the LED strip or row 1551. In some embodiments, the plurality of LEDs may have a length of 2.84 inches or centimeters. In some embodiments, the plurality of LEDs may have a length ranging from 1.5 to 4.5 inches or centimeters.

In some embodiments, a cash sterilization device includes a sterilization device case, the sterilization device case having an opening on one side and a cap assembly; and an internal sterilization assembly, the internal sterilization device including an opening, wherein the internal sterilization is inserted into the opening of the sterilization device case, the cap assembly is attached to cover the internal sterilization within the sterilization device case, and wherein the opening of the sterilization device case is aligned with the opening of the internal sterilization assembly. In some embodiments, the height of the cash sterilization device may have a height ranging from 1 to 3 inches, a length ranging from 2 inches to 4.5 inches, and a width ranging from 4 to 7 inches.

In some embodiments, the internal sterilization assembly may include a cap assembly, an LED assembly, and a sterilization component main body and wherein the LED assembly is inserted into a cap assembly opening and is inserted a sterilization component main body opening. In some embodiments, the cap assembly opening may be rectangular in shape and wherein the cap assembly may further include a driving gear assembly guide and a motor assembly guide. In some embodiments, the sterilization component main body includes a motor assembly, a motor roller gear assembly, and a driving roller gear assembly and wherein the motor assembly may further include a shaft. In some embodiments, the motor roller gear assembly may be connected to the shaft of the motor assembly. In some embodiments, the motor roller gear assembly may include a motor gear and a motor roller and the driving roller gear assembly may include a driving gear and a driving roller, and the motor gear is connected or engaged with the driving gear. In some embodiments, the motor assembly may be configured to rotate when activated, the shaft may be configured to rotate when the motor assembly is activated, and the motor roller gear assembly and the driving roller gear assembly may be configured to rotate when the shaft rotates due to the driving gear being engaged with the motor gear.

In some embodiments, the sterilization component main body may further include a motor and LED cover, wherein the motor assembly may be inserted into the motor and LED cover, and the motor assembly shaft extends from motor and LED cover. In some embodiments, one end of the LED assembly is inserted into the motor and LED cover and the other end is inserted into the cap assembly opening. In some embodiments, the motor and LED cover may further include a drive roller guide and an end of the drive roller is positioned around the drive roller guide. In some embodiments, the LED assembly includes two LED printed circuit boards and the motor and LED cover includes an upper LED cover assembly and a lower LED cover assembly, and a first LED printed circuit board is inserted into the upper LED cover assembly and a second LED printed circuit board is inserted into the lower LED cover assembly. In some embodiments, the positioning of the first LED printed circuit board in the upper LED cover assembly with respect to the second LED printed circuit board in the lower LED cover assembly may create an LED opening, the LED opening aligned with the opening of the sterilization device case. In some embodiments, the motor and LED cover may include one or more (e.g., two as illustrated in FIGS. 15D, wiring holes on an opposite end from where the motor assembly is inserted into the motor cover and LED cover, the two wiring holes to receive power wires and/or control wires. In some embodiments, the cash sterilization device may include a separate power supply, the separate power supply connected to power wires, the power wires configured to provide power to the cash sterilization device. In some embodiments, the cash sterilization device may further include one or more processors or controllers, the one or more processors or controllers coupled to the control wires, the one or more processors or controllers configured to control operations of the cash sterilization device.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein, Examples of memory devices comprise, without limitation. Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample, Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

As used herein, the term "or" is used inclusively to refer items in the alternative and in combination.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

The invention claimed is:

1. A cash sterilization device, comprising:
a sterilization device case, the sterilization device case having an opening on one side and a cap assembly; and
an internal sterilization assembly, the internal sterilization assembly including an opening, wherein the internal sterilization assembly is inserted into the opening of the sterilization device case, the cap assembly is attached to cover the internal sterilization assembly within the sterilization device case,
wherein the internal sterilization assembly further includes a cap assembly, an LED assembly, and a sterilization component main body and wherein the LED assembly is inserted into a cap assembly opening and is inserted into a sterilization component main body opening, wherein the cap assembly opening is rectangular in shape and wherein the cap assembly further includes a driving gear assembly guide and a motor assembly guide,
wherein the sterilization component main body further includes a motor assembly, a motor roller gear assembly, and a driving roller gear assembly and wherein the motor assembly further includes a shaft, the motor roller gear assembly includes a motor gear and the driving roller gear assembly includes a driving gear and a driving roller, and the motor gear is connected or engaged with the driving gear and the motor roller gear assembly and is connected to the shaft of the motor assembly,
wherein the opening of the sterilization device case is aligned with the opening of the internal sterilization assembly, and
wherein the height of the cash sterilization device includes a height ranging from 1 to 3 inches, a length ranging from 2 inches to 4.5 inches, and a width ranging from 4 to 7 inches.

2. The cash sterilization device of claim 1, wherein the motor assembly is configured to rotate when activated, the shaft is configured to rotate when the motor assembly is activated, and the motor roller gear assembly and the driving roller gear assembly are configured to rotate when the shaft rotates due to the driving gear being engaged with the motor gear.

3. The cash sterilization device of claim 2, wherein the sterilization component main body further includes an LED cover, wherein the motor assembly is inserted into the LED cover, and the shaft extends from the motor assembly and the LED cover.

4. The cash sterilization device of claim 3, wherein one end of the LED assembly is inserted into the motor assembly and the LED cover and the other end is inserted into the cap assembly opening.

5. The cash sterilization device of claim 3, wherein the motor assembly and the LED cover further includes a driving roller guide and an end of the driving roller gear assembly is positioned around the driving roller guide.

6. The cash sterilization device of claim 4, wherein the LED assembly includes two LED printed circuit boards and the motor assembly and the LED cover includes an upper LED cover assembly and a lower LED cover assembly, and a first LED printed circuit board is inserted into the upper LED cover assembly and a second LED printed circuit board is inserted into the lower LED cover assembly.

7. The cash sterilization device of claim 6, wherein the positioning of the first LED printed circuit board in the upper LED cover assembly with respect to the second LED printed circuit board in the lower LED cover assembly creates an LED opening, the LED opening aligned with the opening of the sterilization device case.

8. The cash sterilization device of claim 6, wherein the motor assembly and the LED cover includes two wiring holes on an opposite end from where the motor assembly is inserted into a motor cover and the LED cover, the two wiring holes to receive power wires and/or control wires.

9. The cash sterilization device of claim 8, further including a separate power supply, the separate power supply connected to the power wires, the power wires configured to provide power to the cash sterilization device.

10. The cash sterilization device of claim 8, further including one or more processors or controllers, the one or more processors or controllers coupled to the control wires, the one or more processors or controllers configured to control operations of the cash sterilization device.

* * * * *